US012616715B2

(12) United States Patent
Tung et al.

(10) Patent No.: US 12,616,715 B2
(45) Date of Patent: May 5, 2026

(54) NANOTHERAPY TARGETING RHAMM-POSITIVE TUMORS

(71) Applicant: Cornell University, Ithaca, NY (US)

(72) Inventors: Ching-Hsuan Tung, New York, NY (US); Yi-Chieh Nancy Du, Great Neck, NY (US); Seung Koo Lee, New York, NY (US); Xiang Chen, New York, NY (US)

(73) Assignee: Cornell University, Ithaca, NY (US)

( * ) Notice: Subject to any disclaimer, the term of this patent is extended or adjusted under 35 U.S.C. 154(b) by 631 days.

(21) Appl. No.: 17/920,582

(22) PCT Filed: Apr. 23, 2021

(86) PCT No.: PCT/US2021/028834
§ 371 (c)(1),
(2) Date: Oct. 21, 2022

(87) PCT Pub. No.: WO2021/216997
PCT Pub. Date: Oct. 28, 2021

(65) Prior Publication Data
US 2023/0158061 A1     May 25, 2023

Related U.S. Application Data

(60) Provisional application No. 63/152,536, filed on Feb. 23, 2021, provisional application No. 63/014,508, filed on Apr. 23, 2020.

(51) Int. Cl.
A61K 31/713      (2006.01)
A61K 9/00      (2006.01)
A61K 9/51      (2006.01)

(52) U.S. Cl.
CPC .......... *A61K 31/713* (2013.01); *A61K 9/0019* (2013.01); *A61K 9/5161* (2013.01)

(58) Field of Classification Search
CPC ... A61K 31/713; A61K 9/0019; A61K 9/5161
See application file for complete search history.

(56) References Cited

FOREIGN PATENT DOCUMENTS

WO      WO-2011009624 A1 *   1/2011   .......... A61K 47/549

OTHER PUBLICATIONS

Lee et al.; Versatile Nanodelivery Platform to Maximize siRNA Combination Therapy; Wiley-VCH Verlag GmbH; Macromol. Biosci. 2017, 17, 1600294 (1-7) (Year: 2017).*
Choi et al.; Binary Targeting of siRNA to Hematologic Cancer Cells In Vivo Using Layer-by-Layer Nanoparticles; Wiley-VCH Verlag GmbH; Adv. Funct. Mater. 2019, 29, 1900018 (1-13) (Year: 2019).*
Assmann et al.; The human hyaluronan receptor RHAMM is expressed as an intracellular protein in breast cancer cells; The Company of Biologists Limited; Journal of Cell Science 111, 1685-1694 (1998) (Year: 1998).*

(Continued)

*Primary Examiner* — Robert A Wax
*Assistant Examiner* — John W Lippert, III
(74) *Attorney, Agent, or Firm* — Foley & Lardner LLP

(57) ABSTRACT

The present technology is directed to nanoparticle compositions and methods useful in treating RHAMM-positive cancers. Such nanoparticle compositions include a plurality of nanoparticles where each nanoparticle includes (i) a particle core with an outer surface; a first layer coating the outer surface of the particle core, the first layer including one or both of poly-L-lysine and poly-L-arginine and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including an apoptotic peptide and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm; or (ii) a particle core with an outer surface; a first layer coating the outer surface of the particle core, the first layer including an apoptotic peptide and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including one or both of poly-L-lysine and poly-L-arginine and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm.

20 Claims, 23 Drawing Sheets
Specification includes a Sequence Listing.

(56) References Cited

OTHER PUBLICATIONS

Mele, V.; The hyaluronan-mediated motility receptor RHAMM promotes growth, invasiveness and dissemination of colorectal cancer; Impact Journals; Oncotarget, 2017, vol. 8, (No. 41), pp. 70617-70629 (Year: 2017).*

Google Search; is RHAMM positive cancer is expressed in triple negative breast cancer (Year: 2025).*

Assmann et al., "The human hyaluronan receptor RHAMM is expressed as an intracellular protein in breast cancer cells", Journal of Cell Science, vol. 111, PT 12, 1998, pp. 1685-1694.

Choi et al., "Binary Targeting of siRNA to Hematologic Cancer Cells in Vivo using Layer-by-Layer Nanoparticles", Advanced Functional Materials, vol. 29, No. 20, 2019, pp. 1-27.

Choi et al., "Function and clinical relevance of RHAMM isoforms in pancreatic tumor progression", Molecular Cancer, vol. 18, No. 1, article 92, 2019, pp. 1-7.

International Search Report and Written Opinion on PCT PCT/US2021/028834 Dtd Oct. 13, 2021.

Lee et al., "Versatile nano-delivery platform to maximize siRNA combination therapy", Macromolecular Bioscience, vol. 17, No. 2, 2016, pp. 1-16.

Mele et al., "The hyaluronan-mediated motility receptor RHAMM promotes growth, invasiveness and dissemination of colorectal cancer", Oncotarget, vol. 8, No. 41, 2017, p. 70617-70629.

* cited by examiner

Au/L/siRNA/L/HA

- hyaluronic acid (HA)
- PLL
- siRNA for Bcl-xL or scramble control
- PLL-cy5.5
- Gold (Au)

PLL-cy5.5 (+)    siRNA (−)    PLL (+)    HA (−)

Au    Au/L    Au/L/siB or Au/L/siC    Au/L/siB/L or Au/L/siC/L    Au/L/siB/L/HA or Au/L/siC/L/HA

Without NPs

Au/L/HA

Au/L/siC/L/HA

Au/L/siB/L/HA

CD45⁺ cells

CD8⁺ T cells (gated on CD45⁺ CD3⁺)

CD4⁺ T cells (gated on CD45⁺CD3⁺)

B cells (gated    CD45⁺CD3⁻)

RHAMM$^B$

$P < 0.0001$

NANOTHERAPY TARGETING RHAMM-POSITIVE TUMORS

CROSS-REFERENCE TO RELATED APPLICATIONS

This application is a U.S. National Phase Application under 35 U.S.C. 371 of International Application No. PCT/US2021/028834, filed on Apr. 23, 2021, which claims the benefit of and priority to U.S. Provisional Appl. No. 63/014,508, filed Apr. 23, 2020, and the benefit of and priority to U.S. Provisional Appl. No. 63/152,536, filed Feb. 23, 2021, each of which is incorporated herein by reference in their entireties for any and all purposes.

SEQUENCE LISTING

The instant application contains a Sequence Listing which has been submitted electronically in ASCII format and is hereby incorporated by reference in its entirety. Said ASCII copy, created on Jun. 16, 2021, is named 093873-1314 SL.txt and is 10,196 bytes in size.

FIELD

The present technology is directed to nanoparticle compositions and methods useful in treating RHAMM-positive cancers.

SUMMARY

In an aspect, a method for treating a subject suffering from a RHAMM-positive cancer is provided, where the method includes administering to the subject an effective amount of a nanoparticle composition to treat the RHAMM-positive cancer. The nanoparticle composition of the method includes a plurality of nanoparticles, where each nanoparticle includes a particle core with an outer surface; a first layer coating the outer surface of the particle core, the first layer including one or both of poly-L-lysine and poly-L-arginine and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including an apoptotic peptide and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm.

In an aspect, a nanoparticle composition is provided that includes a plurality of nanoparticles, where each nanoparticle includes a particle core with an outer surface; a first layer coating the outer surface of the particle core, the first layer including one or both of poly-L-lysine and poly-L-arginine and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including an apoptotic peptide and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm.

In an aspect, a method for treating a subject suffering from a RHAMM-positive cancer is provided, where the method includes administering to the subject an effective amount of a nanoparticle composition to treat the RHAMM-positive cancer, where the nanoparticle composition includes a plurality of nanoparticles, and where each nanoparticle includes a particle core with an outer surface; a first layer coating the outer surface of the particle core, the first layer including an apoptotic peptide and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including one or both of poly-L-lysine and poly-L-arginine and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm.

In an aspect, a nanoparticle composition is provided that includes a plurality of nanoparticles, where each nanoparticle includes a particle core with an outer surface; a first layer coating the outer surface of the particle core, the first layer including an apoptotic peptide and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including one or both of poly-L-lysine and poly-L-arginine and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm.

DESCRIPTION OF THE DRAWINGS

FIG. 1A provides the results of Western blot analysis of human RHAMM in mouse PNET N134 and N134-RHAMM[B] cells. FIG. 1B provides representative liver photos from mice injected with N134 and N134-RHAMM[B] cells. $2 \times 10^6$ N134 or N134-RHAMM[B] cells were injected into NSG mice (n=5) through the tail vein. Six weeks later, mice were euthanized to survey for metastatic sites and incidence. FIG. 1C illustrates target-specific uptake of Au/L/HA (0.08 nmol) in N134-RHAMM[B] cells compared to N134 cells (magnification: ×40). FIG. 1D provides the results of Western blot analysis of human RHAMM in human PNET BON1_TGL_shLacZ and BON1_TGL_shRHAMM cells. FIG. 1E illustrates target-specific uptake of Au/L/HA in BON1_TGL_shLacZ cells compared to BON1_TGL_shRHAMM (magnification: ×40). Au, AuNP; L, PLL-Cy5.5.

FIG. 2A provides schematic representation of the experiment design. N134-RHAMM$^B$ cells were seeded on 96-well plate and cultured for one day. Then, various nanocomplexes (siControl (siC) or siBcl-xL (siB): 0.12 μM) were treated for 12 h and further cultured in complete medium after washing cells twice with PBS. At designated time periods (24 h, 48 h, and 72 h after treatment with each nanocomplexes), cell viability assay and caspase 3 assay were performed. FIG. 2B illustrates cell viability of N134-RHAMM$^B$ cells treated with Au/L/siBcl-xL/L/HA. Both untreated cells and Au/L/siC/L/HA, Au/L/HA are used as controls. The cell viability of the untreated N134-RHAMM$^B$ were set as 100%. FIG. 2C illustrates that the activity of caspase 3 based on the cleaved NucView 488 caspase 3 substrate was increased after 48 h treatment with Au/L/siBcl-xL/L/HA in N134-RHAMM$^B$ cells comparing Au/L/HA or Au/L/siC/L/HA treatment or untreated cells. FIG. 2D provides the results of Western blotting analysis of Bcl-xL expression levels in Au/L/siBcl-xL/L/HA treated N134-RHAMM$^B$ cells. Tubulin was used as a control loading. $1 \times 10^6$ cells were seeded. After one day, cells were treated with Au/L/siBcl-xL/L/HA or different nanocomplex controls (Au/L/HA, Au/L/siC/L/HA) for 12 h, and then washed twice with PBS following by additional incubation until 48 h or 72 h.

FIG. 3A provides schematic illustration of the process of preparing multilayered Au/L/siB/K/HA by electrostatic interaction. The negatively charged AuNP core sequentially layered with PLL-Cy5.5 (+), siB (−), KLA-FITC (+), and HA (−) using charge-charge interactions. FIG. 3B illustrates the average size (color bars) and zeta potential (black line) in the preparation of Au/L/siB/K/HA. Au, gold NP; L, PLL-Cy5.5; siB, Bcl-xL siRNA; K, KLA peptide; HA, hyaluronic acid.

FIG. 4C illustrates specific synergistic cytotoxic effect induced by the RHAMM$^B$-targeting combinational nanocomplex, Au/L/siB/K/HA, in PNET cells. Cells were seeded on 96-well plate. After one day, cells were treated with Au/L/siB/K/HA or different nanocomplex controls for 12 h and washed twice with PBS. Cells were then incubated for additional 48 h. Cell viability of the untreated N134-RHAMM$^B$ or N134 cells were set as 100%. KLA: 1.6 μM, siControl: 0.12 μM, siBcl-xL: 0.12 μM. Au, gold NP; L, PLL-Cy5.5; siB, Bcl-xL siRNA; K, KLA peptide; HA, hyaluronic acid.

FIG. 5A illustrates workflow of in vivo study. $5 \times 10^6$ N134-RHAMM$^B$ cells were subcutaneously injected into RIP-TVA mice. When tumors were visible (4 mm³), either Au/L/HA (template particles, 10 nmol) or Au/L/siB/K/HA (therapeutic particles, Bcl-xL siRNA: 0.67 mg/kg, KLA: 2.84 mg/kg) were injected via tail vein, twice weekly for 2 weeks. Mice were euthanized 2 days after final NP treatment. FIG. 5B illustrates tumor size of untreated and Au/L/HA treated control groups versus Au/L/siB/K/HA group. FIG. 5C illustrates tumor weight of untreated and Au/L/HA treated control groups versus Au/L/siB/K/HA group. FIG. 5D illustrates accumulation of the RHAMM$^B$-targeting combinational nanocomplexes in the tumor and major organs. After sacrificing mice, the biodistribution of nanocomplexes was evaluated by optical imaging (IVIS Spectrum) (n≥3 per group). Liv, liver; tum, tumor; spl+pan, spleen and pancreas; lun+her, lung and heart; kid, kidneys; mus, muscle. ****P<0.0001. Au, gold NP; L, PLL-Cy5.5; siB, Bcl-xL siRNA; K, KLA peptide; HA, hyaluronic acid.

FIG. 6A illustrates tumor weight of untreated and Au/L/HA treated groups versus Au/L/siB/K/HA group. $5 \times 10^6$ N134-RHAMM$^B$ cells were subcutaneously injected into RIP-TVA mice. When tumors were visible (4 mm³), either Au/L/HA (template particles, 10 nmol) or Au/L/siB/K/HA (therapeutic particles, Bcl-xL siRNA: 0.67 mg/kg, KLA: 2.84 mg/kg) were injected via tail vein, twice weekly for 1 week. Mice were euthanized 2 days after final NP treatment. (B-F) H&E of tumors (FIG. 6B), immunohistochemical staining of active caspase-3 (FIG. 6C) and Ki67 (FIG. 6D) of the tumors, and H&E of liver (FIG. 6E) and kidney (FIG. 6F) after different treatments. Scale bar, 20 μm. Au, gold NP; L, PLL-Cy5.5; siB, Bcl-xL siRNA; K, KLA peptide-FITC; HA, hyaluronic acid.

5

6

Figure 10A:
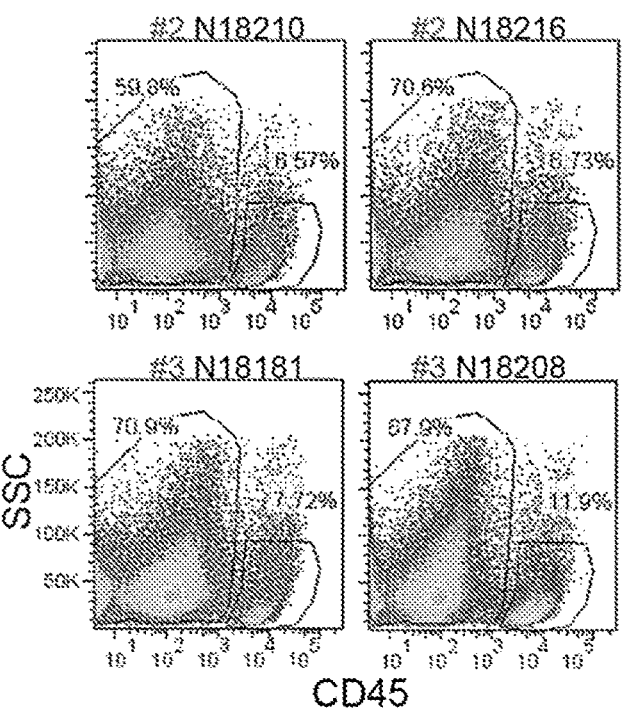
FIGS. 10A-10F provide the results of immune cell profiling of RHAMM$^B$-targeting combinational nanocomplexes treated N134-RHAMM$^B$ tumors. The whole tumors from Au/L/HA treated and Au/L/siB/K/HA treated groups were harvested 2 days after the 4$^{th}$ NP treatment and digested into single cells for immune cell profiling by flow cytometry.
Figure 10B:
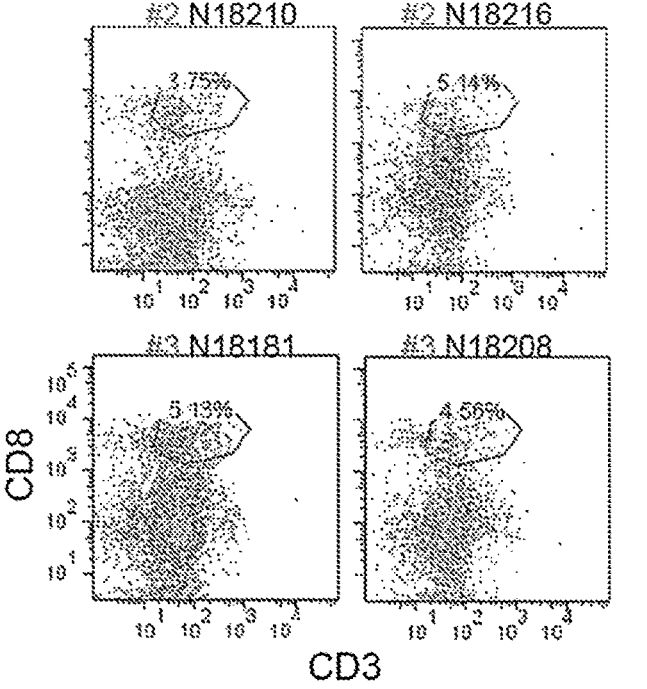
Figure 10C:
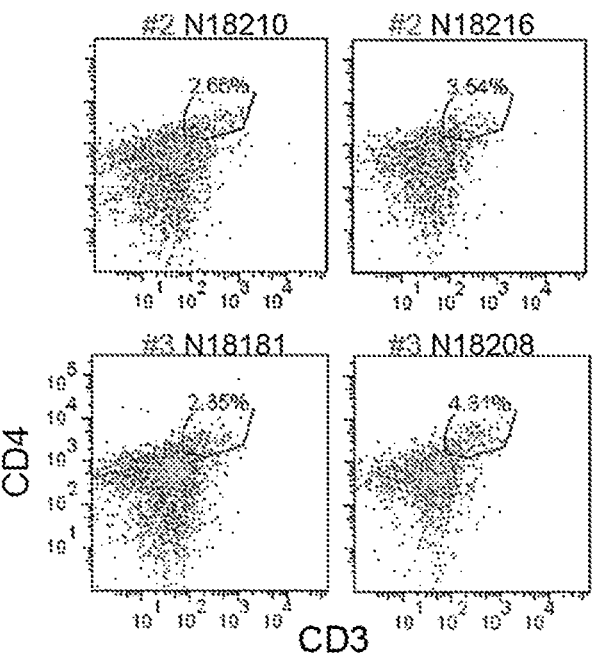
Figure 10D:
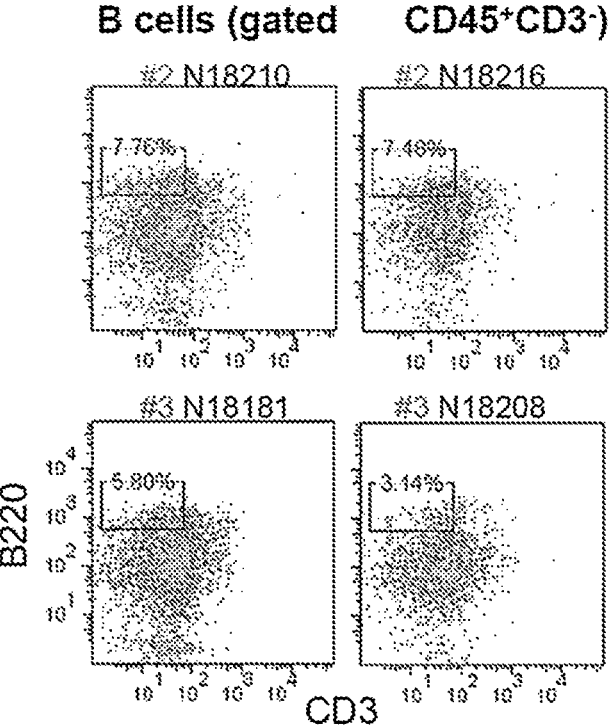
Figure 10E:
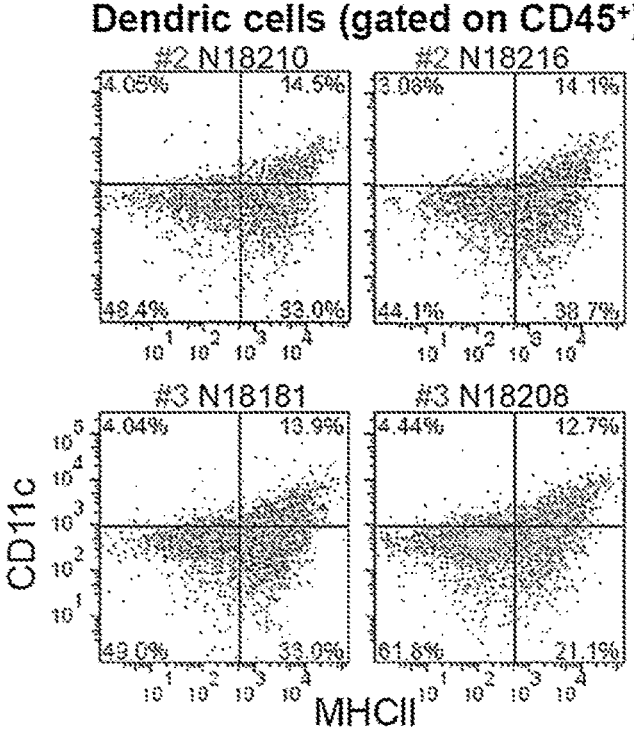
Figure 10F:
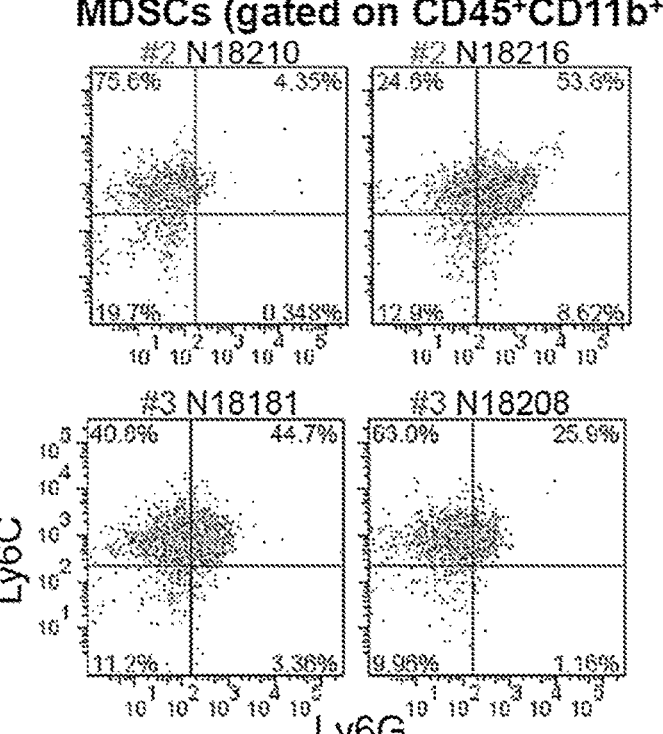

Cells were stained for surface CD45 (FIG. 10A), CD3 (FIGS. 10B-10D), CD8 (FIG. 10B), CD4 (FIG. 10C), B220 (FIG. 10D), MHCII (FIG. 10E), Ly6G (FIG. 10F), and Ly6C (FIG. 10F). Au, gold; L, PLL-Cy5.5; siB, Bcl-xL siRNA; K, KLA peptide; HA, hyaluronic acid.

Figures 11, 12:
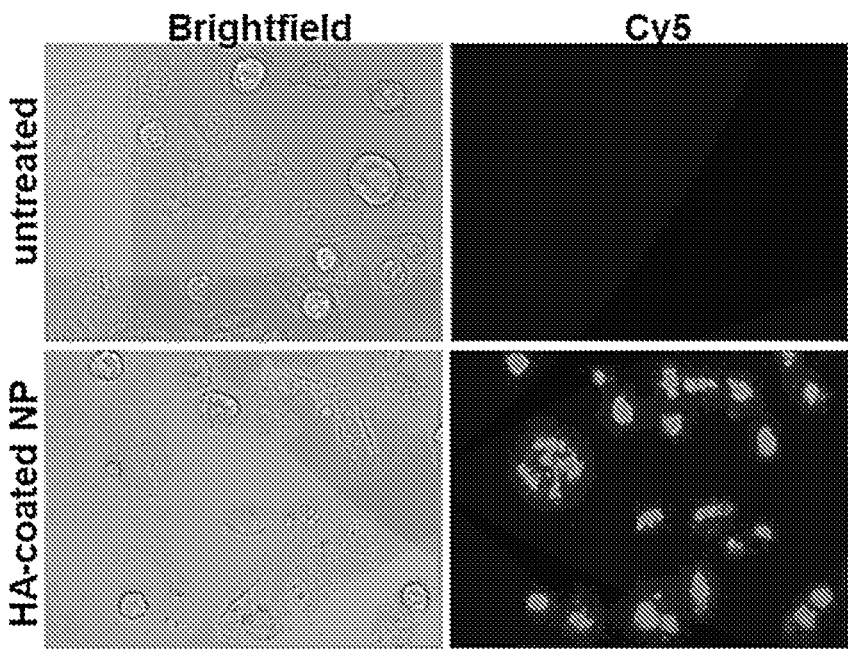

FIG. 11 illustrates RHAMM overexpression in human breast cancer (RHAMM$^B$ expression values from TCGA breast cancer dataset).

FIG. 12 illustrates target-specific delivery of HA-coated nanoparticles (Cy5+) to human breast cancer MDA-MB-231 cells.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 weight %" would be understood to mean "9 weight % to 11 weight %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

The phrase "and/or" as used in the present disclosure and claims will be understood to mean any one of the recited members individually or a combination of any two or more thereof—for example, "A, B, and/or C" would mean "A, B, C, A and B, A and C, or B and C."

As used herein, the term "amino acid" includes naturally-occurring α-amino acids and synthetic α-amino acids (e.g., 2-amino-2-phenylacetic acid, also referred to as phenylgly-cine), as well as α-amino acid analogues and amino acid mimetics that function in a manner similar to the naturally-occurring amino acids. The term further includes both L and D forms of such α-amino acids unless a specific stereoiso-mer is indicated. Naturally-occurring amino acids are those encoded by the genetic code, as well as those amino acids that are later modified, e.g., hydroxyproline, γ-carboxyglu-tamate, and O-phosphoserine. Amino acid analogues refer to compounds that have the same basic chemical structure as a naturally-occurring amino acid, e.g., an α-carbon bearing an organic group, e.g., homoserine, norleucine, methionine sulfoxide, methionine methyl sulfonium. Such analogues may have modified organic groups (e.g., norleucine) or modified peptide backbones, but retain the same basic chemical structure as a naturally-occurring amino acid. Amino acid mimetics refer to chemical compounds that have a structure that is different from the general chemical struc-ture of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the terms "polypeptide," "peptide," and "protein" are used interchangeably herein to mean a polymer comprising two or more amino acids joined to each other by peptide bonds or modified peptide bonds, i.e., peptide isos-teres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-transla-tional processing, or by chemical modification techniques that are well known in the art, as well as synthetic amino acids.

Generally, reference to a certain element such as hydrogen or H is meant to include all isotopes of that element. For example, if an R group is defined to include hydrogen or H, it also includes deuterium and tritium. Compounds compris-ing radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As will be understood by one skilled in the art, for any and all purposes, particularly in terms of providing a written description, all ranges disclosed herein also encompass any and all possible subranges and combinations of subranges thereof. Any listed range can be easily recognized as suffi-ciently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As understood by one of ordinary skill in the art, "molecu-lar weight" (also known as "relative molar mass") is a dimensionless quantity but is converted to molar mass by multiplying by 1 gram/mole or by multiplying by 1 Da—for example, a compound with a weight-average molecular weight of 5,000 has a weight-average molar mass of 5,000 g/mol and a weight-average molar mass of 5,000 Da.

Pharmaceutically acceptable salts of compounds described herein are within the scope of the present tech-nology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. Alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. Arginine, lysine and ornithine). Such salts can be prepared in situ during isolation and purification of the compounds or by separately reacting the purified compound in its free base or free acid form with a suitable acid or base, respectively, and isolating the salt thus formed.

Throughout this disclosure, various publications, patents and published patent specifications are referenced by an identifying citation. Also within this disclosure are Arabic numerals referring to referenced citations, the full bibliographic details of which are provided preceding the claims. The disclosures of these publications, patents and published patent specifications are hereby incorporated by reference into the present disclosure.

The Present Technology

The present technology is directed to nanoparticle compositions and methods useful in treating RHAMM-positive cancers.

In an aspect, a nanoparticle composition is provided that includes a plurality of nanoparticles, where each nanoparticle includes a particle core with an outer surface; a first layer coating the outer surface of the particle core, the first layer including one or both of poly-L-lysine and poly-L-arginine and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including an apoptotic peptide and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm. Accordingly, the plurality of nanoparticles may have an intensity-weighted average diameter as determined by dynamic light scattering of about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225 nm, about 230 nm, about 235 nm, about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, or any range including and/or in between any two of these values. The nanoparticle compositions of the present technology may exist as solvates, especially hydrates. Hydrates may form during manufacture of the nanoparticle compositions, or hydrates may form over time due to the hygroscopic nature of the nanoparticle compositions. Nanoparticle compositions of the present technology may exist as organic solvates as well, including DMF, ether, and alcohol solvates among others. The identification and preparation of any particular solvate is within the skill of the ordinary artisan of synthetic organic or medicinal chemistry. In any embodiment disclosed herein, it may be that the nanoparticle composition further includes water.

In any embodiment disclosed herein, the particle core in the plurality of nanoparticles may have an intensity-weighted average diameter as determined by dynamic light scattering from about 30 nm to about 50 nm. Thus, the particle core in the plurality of nanoparticles may have an intensity-weighted average diameter as determined by dynamic light scattering of about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50 nm, or any range including and/or in between any two of these values. The particle core may be an organic particle core, an inorganic particle core, or a combination thereof. Particle cores may be cores that include one or more of a ceramic, silicon, a glass, mica, graphite, a carbon nanotube, a metal (e.g., gold, silver, platinum, steel, and/or alloys); a metal-coated material, a metal oxide (e.g., maghemite ($\gamma$-$Fe_2O_3$), magnetite ($Fe_3O_4$), feroxyhyte (FeO (OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), or a combination of any two or more thereof), and a polymer (e.g., a poly(arylate), a poly(anhydride), a poly(hydroxy acid), a polyester, a poly(ortho ester), a poly(alkylene oxide), a polycarbonate, a poly(propylene fumerate), a poly(caprolactone), a polyamide, a polyamino acid, a polyacetal, a polylactide, a polyglycolide, a poly(dioxanone), a polyhydroxybutyrate, a polyhydroxyvalyrate, a poly(vinyl pyrrolidone), a polycyanoacrylate, a polyurethane, a polysaccharide, or a combination of any two or more thereof). Accordingly, in any embodiment disclosed herein, the particle core may be a gold particle core. The gold particle core in the plurality of nanoparticles may have an intensity-weighted average diameter as determined by dynamic light scattering from about 30 nm to about 50 nm. Thus, the gold particle core in the plurality of nanoparticles may have an intensity-weighted average diameter as determined by dynamic light scattering of about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50 nm, or any range including and/or in between any two of these values.

In any embodiment disclosed herein, the first layer may have an average thickness of about 30 nm to about 40 nm. Thus, in any embodiment disclosed herein, the first layer may have an average thickness of about 30 nm, about 31 nm, about 32 nm, about 33 nm, about 34 nm, about 35 nm, about 36 nm, about 37 nm, about 38 nm, about 39 nm, about 40 nm, or any range including and/or in between any two of these values. In any embodiment disclosed herein, it may be that the first layer does or does not include a fluorescent dye; in embodiments where the first layer includes a fluorescent dye, the fluorescent dye may be covalently conjugated to poly-L-lysine and/or covalently conjugated to poly-L-arginine.

In any embodiment disclosed herein, the first layer may include poly-L-lysine with a weight-average molecular weight of about 30,000 to about 70,000. Thus, in any embodiment disclosed herein, the first layer may include poly-L-lysine with a weight-average molecular weight of about 30,000, about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, about 50,000, about 51,000, about 52,000, about 53,000, about 54,000, about 55,000, about 56,000, about 57,000, about 58,000, about 59,000, about 60,000, about 61,000, about 62,000, about 63,000, about 64,000, about 65,000, about 66,000, about 67,000, about 68,000, about 69,000, about 70,000, or any range including and/or in between any two of these values.

In any embodiment disclosed herein, the second layer may have an average thickness of about 6 nm to about 20 nm. Thus, in any embodiment disclosed herein, the second layer may have an average thickness of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, or any range including and/or in between any two of these values. In any embodiment disclosed herein, the second layer may include one or more siRNAs having the sequence of any one of

```
                                        (SEQ ID NO. 2)
5'-GGUAUUGGUGAGUCGGAUCdTdT-3', (SEQ ID NO. 3)
5'-GAUCCGACUCACCAAUACCdTdT-3', (SEQ ID NO. 16)
5'-CAGGGACAGCATATCAGAG-3', (SEQ ID NO. 17)
5'-CTCTGATATGCTGTCCCTG-3', (SEQ ID NO. 18)
5'-UCACUAAACUGACUCCAGCUGUAUC-3', (SEQ ID NO. 19)
5'-GAUACAGCUGGAGUCAGUUUAGUGA-3', (SEQ ID NO. 20)
5'-CCCAGUGCCAUCAAUGGCAACCCAU-3', (SEQ ID NO. 21)
5'-AUGGGUUGCCAUUGAUGGCACUGGG-3', (SEQ ID NO. 22)
5'-GCAGUUUGGAUGCCCGGGAGGUGAU-3', (SEQ ID NO. 23)
5'-AUCACCUCCCGGGCAUCCAAACUGC-3', (SEQ ID NO. 24)
5'-AACAGGGACAGCATATCAGAGCTdTdT-3', (SEQ ID NO. 25)
5'-AGCUCUGAUAUGCUGUCCCUGUUdTdT-3', (SEQ ID NO. 26)
5'-GGAGAUGCAGGUAUUGGUG-3', (SEQ ID NO. 27)
5'-CACCAAUACCUGCAUCUCC-3',
```

10

```
                                        (SEQ ID NO. 28)
5'-UGACCAGACACUGACCAUC-3', (SEQ ID NO. 29)
5'-GAUGGUCAGUGUCUGGUCA-3', (SEQ ID NO. 30)
5'-CAGGGACAGCAUAUCAGAGdTdT-3', (SEQ ID NO. 31)
5'-CUCUGAUAUGCUGUCCCUGdTdT-3', (SEQ ID NO. 32)
5'-AGUUUCGAGACUAUACGAC-3', (SEQ ID NO. 33)
5'-GUCGUAUAGUCUCGAAACU-3', (SEQ ID NO. 34)
5'-GCAGCUUGGAUGGCCACUUdTdT-3',
and (SEQ ID NO. 35)
5'-AAGUGGCCAUCCAAGCUGCdAdG-3'.
```

In any embodiment disclosed herein, the third layer may have an average thickness of about 6 nm to about 20 nm. Thus, in any embodiment disclosed herein, the third layer may have an average thickness of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, or any range including and/or in between any two of these values. In any embodiment disclosed herein, it may be that the third layer does or does not include a fluorescent dye; in embodiments where the third layer includes a fluorescent dye, the fluorescent dye may be covalently conjugated to an apoptotic peptide. In any embodiment disclosed herein, the third layer may include one or more apoptotic peptides having the sequence of any one of

```
                                        (SEQ ID NO. 1)
KLAKLAKKLAKLAKKLAKLAKKLAKLAK, (SEQ ID NO. 6)
FLGALFKALSKLL, (SEQ ID NO. 7)
RAALAVVLGRGGPR, (SEQ ID NO. 8)
RDGDSCRGGGPV, (SEQ ID NO. 9)
THRPPMWSPVWPGGGKLLLKLLKKLLKLLKKK, (SEQ ID NO. 10)
c(LKLKKFKKLQ), (SEQ ID NO. 11)
CRGDCGGKWCFRVCYRGICYRRCR, (SEQ ID NO. 12)
GIGKFLHSAKKFGKAFVGEIMNS-NH₂, (SEQ ID NO. 13)
N-myristoyl-PSQSK(εN-4-bromobenzoyl)SK
(εN-4-bromobenzoyl)A, (SEQ ID NO. 14)
A₉K,
and (SEQ ID NO. 15)
KLAKLAKKLAKLAKKLAKLAK.
```

In any embodiment disclosed herein, the fourth layer may have an average thickness of about 10 nm to about 40 nm. Thus, in any embodiment disclosed herein, the fourth layer may have an average thickness of, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28, about 29 nm, about 30 nm, about 31 nm, about 32 nm, about 33 nm, about 34 nm, about 35 nm, about 36 nm, about 37 nm, about 38 nm, about 39 nm, about 40 nm, or any range including and/or in between any two of these values. In any embodiment disclosed herein, the fourth layer may include sodium hyaluronate. In any embodiment disclosed herein, the fourth layer may include sodium hyaluronate with a weight-average molecular weight of about 100,000, about 105,000, about 110,000, about 115,000, about 120,000, about 125,000, about 130,000, about 135,000, about 140,000, about 145,000, about 150,000, or any range including and/or in between any two of these values.

In an aspect, a nanoparticle composition is provided that includes a plurality of nanoparticles, where each nanoparticle includes a particle core with an outer surface; a first layer coating the outer surface of the particle core, the first layer including an apoptotic peptide and optionally including a fluorescent dye; a second layer coating the first layer, the second layer including one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1); a third layer coating the second layer, the third layer including one or both of poly-L-lysine and poly-L-arginine and optionally including a fluorescent dye; and a fourth layer coating the third layer, the fourth layer including hyaluronic acid or a pharmaceutically acceptable salt thereof (HA); and where the plurality of nanoparticles has an intensity-weighted average diameter as determined by dynamic light scattering from about 100 nm to about 300 nm. Accordingly, the plurality of nanoparticles may have an intensity-weighted average diameter as determined by dynamic light scattering of about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225 nm, about 230 nm, about 235 nm, about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, or any range including and/or in between any two of these values. The nanoparticle compositions of the present technology may exist as solvates, especially hydrates. Hydrates may form during manufacture of the nanoparticle compositions, or hydrates may form over time due to the hygroscopic nature of the nanoparticle compositions. Nanoparticle compositions of the present technology may exist as organic solvates as well, including DMF, ether, and alcohol solvates among others. The identification and preparation of any particular solvate is within the skill of the ordinary artisan of synthetic organic or medicinal chemistry. In any embodiment disclosed herein, it may be that the nanoparticle composition further includes water.

In any embodiment disclosed herein, the particle core in the plurality of nanoparticles may have an intensity-weighted average diameter as determined by dynamic light scattering from about 30 nm to about 50 nm. Thus, the particle core in the plurality of nanoparticles may have an intensity-weighted average diameter as determined by dynamic light scattering of about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50 nm, or any range including and/or in between any two of these values. The particle core may be an organic particle core, an inorganic particle core, or a combination thereof. Particle cores may be cores that include one or more of a ceramic, silicon, a glass, mica, graphite, a carbon nanotube, a metal (e.g., gold, silver, platinum, steel, and/or alloys); a metal-coated material, a metal oxide (e.g., maghemite ($\gamma$-Fe$_2$O$_3$), magnetite (Fe$_3$O$_4$), feroxyhyte (FeO (OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), or a combination of any two or more thereof), and a polymer (e.g., a poly(arylate), a poly(anhydride), a poly(hydroxy acid), a polyester, a poly(ortho ester), a poly(alkylene oxide), a polycarbonate, a poly(propylene fumerate), a poly(caprolactone), a polyamide, a polyamino acid, a polyacetal, a polylactide, a polyglycolide, a poly(dioxanone), a polyhydroxybutyrate, a polyhydroxyvalyrate, a poly(vinyl pyrrolidone), a polycyanoacrylate, a polyurethane, a polysaccharide, or a combination of any two or more thereof). Accordingly, in any embodiment disclosed herein, the particle core may be a gold particle core. The gold particle core in the plurality of nanoparticles may have an intensity-weighted average diameter as determined by dynamic light scattering from about 30 nm to about 50 nm. Thus, the gold particle core in the plurality of nanoparticles may have an intensity-weighted average diameter as determined by dynamic light scattering of about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50 nm, or any range including and/or in between any two of these values.

In any embodiment disclosed herein, the first layer may have an average thickness of about 6 nm to about 20 nm. Thus, in any embodiment disclosed herein, the first layer may have an average thickness of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, or any range including and/or in between any two of these values. In any embodiment disclosed herein, it may be that the first layer does or does not include a fluorescent dye; in embodiments where the first layer includes a fluorescent dye, the fluorescent dye may be covalently conjugated to an apoptotic peptide. In any embodiment disclosed herein, the first layer may include one or more apoptotic peptides having the sequence of any one of

```
                                        (SEQ ID NO. 1)
    KLAKLAKKLAKLAKKLAKLAKKLAKLAK, (SEQ ID NO. 6)
    FLGALFKALSKLL, (SEQ ID NO. 7)
    RAALAVVLGRGGPR,
```

-continued (SEQ ID NO. 8)
RDGDSCRGGGPV, (SEQ ID NO. 9)
THRPPMWSPVWPGGGKLLLKLLKKLLKLLKKK, (SEQ ID NO. 10)
c(LKLKKFKKLQ), (SEQ ID NO. 11)
CRGDCGGKWCFRVCYRGICYRRCR, (SEQ ID NO. 12)
GIGKFLHSAKKFGKAFVGEIMNS-NH$_2$, (SEQ ID NO. 13)
N-myristoyl-PSQSK(εN-4-bromobenzoyl)SK (εN-4-bromobenzoyl)A, (SEQ ID NO. 14)
A$_9$K,
and (SEQ ID NO. 15)
KLAKLAKKLAKLAKKLAKLAK.

In any embodiment disclosed herein, the second layer may have an average thickness of about 6 nm to about 20 nm. Thus, in any embodiment disclosed herein, the second layer may have an average thickness of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, or any range including and/or in between any two of these values. In any embodiment disclosed herein, the second layer may include one or more siRNAs having the sequence of any one of (SEQ ID NO. 2)
5'-GGUAUUGGUGAGUCGGAUCdTdT-3', (SEQ ID NO. 3)
5'-GAUCCGACUCACCAAUACCdTdT-3', (SEQ ID NO. 16)
5'-CAGGGACAGCATATCAGAG-3', (SEQ ID NO. 17)
5'-CTCTGATATGCTGTCCCTG-3', (SEQ ID NO. 18)
5'-UCACUAAACUGACUCCAGCUGUAUC-3', (SEQ ID NO. 19)
5'-GAUACAGCUGGAGUCAGUUUAGUGA-3', (SEQ ID NO. 20)
5'-CCCAGUGCCAUCAAUGGCAACCCAU-3', (SEQ ID NO. 21)
5'-AUGGGUUGCCAUUGAUGGCACUGGG-3', (SEQ ID NO. 22)
5'-GCAGUUUGGAUGCCCGGGAGGUGAU-3', (SEQ ID NO. 23)
5'-AUCACCUCCCGGGCAUCCAAACUGC-3', (SEQ ID NO. 24)
5'-AACAGGGACAGCATATCAGAGCTdTdT-3', (SEQ ID NO. 25)
5'-AGCUCUGAUAUGCUGUCCCUGUUdTdT-3', -continued (SEQ ID NO. 26)
5'-GGAGAUGCAGGUAUUGGUG-3', (SEQ ID NO. 27)
5'-CACCAAUACCUGCAUCUCC-3', (SEQ ID NO. 28)
5'-UGACCAGACACUGACCAUC-3', (SEQ ID NO. 29)
5'-GAUGGUCAGUGUCUGGUCA-3', (SEQ ID NO. 30)
5'-CAGGGACAGCAUAUCAGAGdTdT-3', (SEQ ID NO. 31)
5'-CUCUGAUAUGCUGUCCCUGdTdT-3', (SEQ ID NO. 32)
5'-AGUUUCGAGACUAUACGAC-3', (SEQ ID NO. 33)
5'-GUCGUAUAGUCUCGAAACU-3', (SEQ ID NO. 34)
5'-GCAGCUUGGAUGGCCACUUdTdT-3',
and (SEQ ID NO. 35)
5'-AAGUGGCCAUCCAAGCUGCdAdG-3'.

In any embodiment disclosed herein, the third layer may have an average thickness of about 30 nm to about 40 nm. Thus, in any embodiment disclosed herein, the third layer may have an average thickness of about 30 nm, about 31 nm, about 32 nm, about 33 nm, about 34 nm, about 35 nm, about 36 nm, about 37 nm, about 38 nm, about 39 nm, about 40 nm, or any range including and/or in between any two of these values. In any embodiment disclosed herein, it may be that the third layer does or does not include a fluorescent dye; in embodiments where the third layer includes a fluorescent dye, the fluorescent dye may be covalently conjugated to poly-L-lysine and/or covalently conjugated to poly-L-arginine.

In any embodiment disclosed herein, the third layer may include poly-L-lysine with a weight-average molecular weight of about 30,000 to about 70,000. Thus, in any embodiment disclosed herein, the third layer may include poly-L-lysine with a weight-average molecular weight of about 30,000, about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, about 50,000, about 51,000, about 52,000, about 53,000, about 54,000, about 55,000, about 56,000, about 57,000, about 58,000, about 59,000, about 60,000, about 61,000, about 62,000, about 63,000, about 64,000, about 65,000, about 66,000, about 67,000, about 68,000, about 69,000, about 70,000, or any range including and/or in between any two of these values.

In any embodiment disclosed herein, the fourth layer may have an average thickness of about 10 nm to about 40 nm. Thus, in any embodiment disclosed herein, the fourth layer may have an average thickness of, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28, about 29 nm, about 30 nm, about 31 nm, about 32 nm, about 33 nm, about 34 nm, about 35 nm, about 36 nm, about 37 nm, about 38 nm, about 39 nm, about 40 nm, or any range including and/or in between any two of these values. In any embodiment disclosed herein, the fourth layer may include sodium hyaluronate. In any embodiment disclosed herein, the fourth layer may include sodium hyaluronate with a weight-average molecular weight of about 100,000, about 105,000, about 110,000, about 115,000, about 120,000, about 125,000, about 130,000, about 135,000, about 140, 000, about 145,000, about 150,000, or any range including and/or in between any two of these values.

In any aspect or embodiment disclosed herein (also referred to as "in any embodiment disclosed herein" or the like), it may be that the nanoparticle composition does not include a fluorescent dye.

The present technology also provides compositions and medicaments comprising any one of the aspects and embodiments of the nanoparticle compositions of the present technology and a pharmaceutically acceptable carrier or one or more excipients or fillers (collectively referred to as "pharmaceutically acceptable carrier" unless otherwise specified). The compositions may be used in the methods and treatments described herein. The present technology also provides pharmaceutical compositions including a pharmaceutically acceptable carrier and an effective amount of a nanoparticle composition of any one of the aspects and embodiments of the nanoparticle compositions of the present technology for treating a RHAMM-positive cancer. The present technology also provides methods for treating a subject suffering from a RHAMM-positive cancer, wherein the method includes administering to the subject an effective amount of a nanoparticle composition of any aspect or embodiment herein to treat the RHAMM-positive cancer (or administering to the subject a pharmaceutical composition or medicament of any aspect or embodiment herein). In any aspect or embodiment herein, the RHAMM-positive cancer may overexpress RHAMM. In any aspect or embodiment herein, the RHAMM-positive cancer may be a RHAMM$^B$-positive cancer (such as a RHAMM$^B$-positive cancer overexpressing RHAMM$^B$). In any aspect or embodiment herein, a solid tumor in the subject may include the RHAMM-positive cancer (e.g., a solid tumor in the subject may include the RHAMM$^B$-positive cancer). In any aspect or embodiment herein, the RHAMM-positive cancer may be a metastatic cancer (e.g., in any aspect or embodiment herein, the RHAMM$^B$-positive cancer may be a metastatic cancer). In any aspect or embodiment herein, the RHAMM-positive cancer (e.g., the RHAMM$^B$-positive cancer) may include one or more of a colon cancer, a colorectal cancer, a gastric cancer, an endometrial cancer, a prostate cancer, a breast cancer, a brain cancer, an ovarian cancer, a pancreatic cancer, and a lung cancer. In any aspect or embodiment herein, the RHAMM-positive cancer (e.g., the RHAMM$^B$-positive cancer) may include a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of e.g., one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer. Another example of an effective amount includes amounts or dosages that are capable of reducing symptoms associated with e.g., one or more of one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer, such as, for example, reduction in proliferation and/or metastasis. An effective amount of a nanoparticle composition of the present technology may include an amount sufficient to enable detection of binding of nanoparticles of the nanoparticle composition to a target of interest including, but not limited to, one or more of one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer.

As used herein, a "subject" or "patient" is a mammal, such as a cat, dog, rodent or primate. Typically the subject is a human, and, preferably, a human suffering from or suspected of suffering from one or more of one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer. The term "subject" and "patient" can be used interchangeably.

In any aspect or embodiment herein, the administration may include oral administration, parenteral administration, intravenous administration, intratumoral administration, or nasal administration. In any of these embodiments, the administration may include subcutaneous injections, intravenous injections, intratumoral injections, intraperitoneal injections, or intramuscular injections. The methods of the present technology may also include administering, either sequentially or in combination with one or more nanoparticle compositions of the present technology, a conventional therapeutic agent in an amount that can potentially or synergistically be effective for the treating of one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer.

In any of the aspects and embodiments of the present technology described herein, the pharmaceutical composition may be packaged in unit dosage form. The unit dosage form is effective in treating one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer. Generally, a unit dosage including a nanoparticle composition of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a nanoparticle composition of the present technology may vary from $1\times10^4$ g/kg to 1 g/kg, preferably, $1\times10^{-3}$ g/kg to 1.0 g/kg. Dosage of a nanoparticle composition of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges. suppositories. patches. nasal sprays, injectables, implantable sustained-release formulations, mucoadherent films, topical varnishes, lipid complexes, etc.

The pharmaceutical compositions may be prepared by mixing one or more nanoparticle compositions of the present technology with pharmaceutically acceptable carriers, excipients, binders, diluents or the like to prevent and treat disorders associated with cancer (e.g., one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer). The compositions of the present technology may be used to prepare formulations and medicaments that treat e.g., one or more of a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, and a metastatic cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, intratumoral, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more nanoparticle compositions of the instant present technology with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Nanoparticle compositions of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular nanoparticle composition, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and non-aqueous (e.g., in a fluorocarbon propellant) aerosols are typically used for delivery of nanoparticle compositions of the present technology by inhalation.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. The instant compositions may also include, for example, micelles or liposomes, or some other encapsulated form.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For the indicated condition, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The examples herein are provided to illustrate advantages of the present technology and to further assist a person of ordinary skill in the art with preparing or using the nanoparticle compositions of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Examples

Materials and Methods

Chemicals and Reagents

Bcl-xL siRNA, poly-L-lysine (PLL) (MW=30,000-70,000 g/mol), diethyl pyrocarbonate (DEPC)-treated water were obtained from Sigma-Aldrich (St. Louis, MO). Bare AuNPs (size: 40 nm) were purchased from BB International (Cardiff, UK), Amersham Cy5.5 Mono NHS Ester was from GE Healthcare (Buckinghamshire, UK), Amicon Ultracel membranes (10 kDa) were from Millipore (Billerica, MA), and sodium hyaluronate (HA) (MW=100-150 kDa) was from Lifecore Biomedical (Chaska, MN). KLA peptide was synthesized as described [23].

Preparation of PLL-Cy5.5

0.08 mg of Cy5.5 in 100 µL water was mixed with 0.2 mg of PLL in 1 mM 100 µL NaHCO$_3$ in the dark at room temperature for 30 min (vortexed every 10 min) and filtered through molecular-weight cutoff membrane filters (10 kDa, Millipore). The resulting PLL-Cy5.5 was collected and washed several times with sterilized water until the color of the filtrate was clear. The loading ratio of Cy5.5 per PLL was calculated based on the absorbance of Cy5.5 (molar extinction coefficients=250,000 m$^{-1}$ cm$^{-1}$ at 678 nm). The Cy5.5/PLL ratio was 4/1.

Preparation of RHAMM-Targeting AuNPs

PLL-Cy5.5, Bcl-xL siRNA, amphipathic antimicrobial peptide KLA and HA were deposited onto the surface of AuNPs (40 nm) using previous modified layer-by-layer fabrication method [23, 24]. For a strong layer-to-layer affinity, a previously validated long KLA peptide (28-mer: KLAKLAKKLAKLAKKLAKLAKKLAKLAK (SEQ ID NO. 1)) was used in the formulation [23]. The sequences of siRNA against Bcl-xL [25] are sense strand: 5'-GGUAUUG-GUGAGUCGGAUCdTdT-3' (SEQ ID NO. 2), antisense strand: 5'-GAUCCGACUCACCAAUACCdTdT-3' (SEQ ID NO. 3), and of scramble control siRNA [25] are sense strand: 5'-UAGGGGUUGCGACGUUUAGdTdT-3' (SEQ ID NO. 4), antisense strand: 5'-CUAAACGUCGCAACCC-CUAdTdT-3' (SEQ ID NO. 5). AuNPs (3.15×10$^9$ particles in 0.7 mL) were added dropwisely onto a PLL-Cy5.5 solution (16.2 nmol in 0.5 mL). After incubating for 30 min in the dark with gentle shaking, the solution was centrifuged for 30 min at 16,100 g using a micro centrifuge (Eppendorf, Hauppauge, NY). The supernatant was removed, and the gel-like pellet was re-suspended with DEPC-treated water and centrifuged for 30 min at 16,100 g. PLL-Cy5.5 coated AuNPs were stored in DEPC-treated water after additional wash. The next polyelectrolyte layer was attached by adding PLL-Cy5.5 coated AuNPs (in 0.5 mL of pure water) to the Bcl-xL siRNA solution (4.0 nmol, 0.5 mL). The reaction solution was incubated in the dark for 30 min with gentle shaking, followed by three washes. The deposition procedures were repeated sequentially with KLA solution (62.5 nmol, 0.5 mL) and HA solution (8 mg/mL, 0.5 mL) in DEPC-treated water, to have a total of 4 layers of polyelectrolytes (PLL-Cy5.5, Bcl-xL siRNA, KLA and HA). The sizes and zeta potentials of each AuNPs in water were measured using a ZetaPALS (Brookhaven, Holtsville, NY) according to the manufacturer's instructions. The amount of Bcl-xL siRNA and KLA in each nanocomplex was calculated by measuring the concentration of Bcl-xL siRNA or fluorescein isothiocyanate (FITC)-labelled KLA (KLA-FITC) in the supernatant before and after the coating using a spectrophotometer (Cary 60 UV-Vis, Agilent, Santa Clara, CA). The prepared RHAMM$^B$-targeting nanocomplexes were stored in DEPC-treated water at 4° C. and used within 2 weeks. Other control particles were prepared following the same procedures. Their names and detail compositions were listed in Table 1.

TABLE 1

| | Layer 1 (+) | Layer 2 (−) | Layer 3 (+) | Layer 4 (−) |
|---|---|---|---|---|
| Au/K | KLA* | | | |
| Au/L/HA | PLL* | HA | | |
| Au/L/siB/L | PLL* | Bcl-xL siRNA | PLL | |
| Au/L/siC/L | PLL* | Scramble control siRNA | PLL | |
| Au/L/siB/K | PLL* | Bcl-xL siRNA | KLA* | |
| Au/L/siB/K/HA | PLL* | Bcl-xL siRNA | KLA* | HA |

*For tracking purpose, KLA and PLL were labeled by FITC and Cy5.5, respectively.

Cell Culture and Western Blot Analysis

Generation of N134 cell line has been described [15, 26]. RHAMM$^B$ overexpressing cell line, N134-RHAMM$^B$, was generated using RCASBP as described [27, 28]. BON1_TGL_shLacZ and BON1_TGL_shRHAMM cells were generated in the previous study [18]. Cells were cultured in Dulbecco's modified Eagle's medium (DMEM) supplemented with 10% fetal bovine serum (FBS), 2 mM L-glutamine, and penicillin/streptomycin.

For Western blot analysis, cell extracts were separated on 10% SDS-PAGE and transferred to nitrocellulose membrane (GE Healthcare). Blots were blocked with 5% (weight/volume) non-fat milk in TBST buffer for 1 h, and incubated at 4° C. overnight with one of the following primary antibodies at 1:1,000 dilution: RHAMM (Abcam, ab108339), Bcl-xL (Cell signalling, #2764) and β-tubulin (Cell signalling, #2128). The next day, blots were washed with TBST and incubated with secondary antibody (GE Healthcare, #NA934V) at 1:5,000 dilution for 1 h at room temperature. Bands were visualized using ECL™ Prime Western Blotting System (GE Healthcare).

Live Cell Imaging of CD44

5,000 cells per well were seeded with 10% FBS-containing DMEM in 96-well flat clear bottom black polystyrene TC-treated microplates (Corning Life Sciences, #3603), and incubated for 48 h. AlexaFluor 488 conjugated anti-human/ mouse CD44 antibody (1:50 dilution, Molecular probes, A25528) was directly added into the cell culture medium of the cells to be stained. After incubation for 30 min at 37° C., the cells were washed with FluoroBrite™ DMEM (Thermofisher, Waltham, MA) and stained with NucBlue Live Cell Stain ReadyProbes reagent (1:50 dilution, Thermofisher, R37605) for 15 min at 37° C. Fluorescence images were acquired using a Lionheart FX Automated Microscope with magnification ×20 (BioTek).

Cellular Uptake of HA-Coated AuNPs (Au/L/HA)

To visualize the cellular uptake, PLL was labeled with a Cy5.5 fluorescent dye. First, cells (N134, N134-RHAMM$^B$ BON1_TGL_shLacZ, or BON1_TGL_shRHAMM) were seeded on a 96-well black clear-bottom culture plate (Corning Life Sciences, #3603) at a density of $2 \times 10^4$ cells per well. After one day, the culture medium was replaced with Au/L/HA (0.08 nmol) containing medium for 12 h. Cells were washed twice with PBS and observed with an EVOS FL Auto Cell Imaging System (Life Technologies, Carlsbad, CA).

Live Cell Caspase 3 Assay

N134-RHAMM$^B$ cells were seeded on μ-Plate 96 Well Black (ibidi GmbH, #89626) at a density of $4 \times 10^4$ cells per well. After 24 h incubation, the culture medium was replaced with various nanocomplexes (siControl or siBcl-xL: 0.12 μM) containing medium. After 12 h incubation, cells were washed twice with PBS and further cultured in complete medium. At designated time periods (24 h, 48 h, and 72 h after treatment with each nanocomplexes), cells were replaced with medium containing 5 μM NucView 488 caspase 3 substrate (Biotium Inc., #10403). After 30 min incubation at room temperature, cells were observed directly in medium containing substrate by an EVOS FL Auto Cell Imaging System (Life Technologies) using filter sets for green fluorescence (Ex/Em: 485/515 nm).

In Vitro Imaging of the RHAMM$^B$-Targeting Combinational Nanocomplexes

A Cy5.5 fluorochrome and FITC was conjugated with PLL and KLA peptide, respectively, for fluorescence imaging. Briefly, N134 or N134-RHAMM$^B$ cells were seeded on a 96-well black clear-bottom culture plate (Corning Life Sciences, #3603) at a density of $2 \times 10^4$ cells per well. After one day, the culture medium was replaced with various nanocomplexes (KLA: 1.6 μM, siControl or siBcl-xL: 0.12 μM) containing medium, and further cultured for 12 h. Cells were then washed twice with PBS, incubated for additional 48 h, and imaged with an EVOS FL Auto Cell Imaging System (Life Technologies).

Cell Viability/Cytotoxicity Assay

N134 or N134-RHAMM$^B$ cells were seeded on 96-well culture plates at a density of $2 \times 10^4$ cells per well. One day later, the culture medium was replaced with various nanocomplexes (KLA: 1.6 μM, siControl or siBcl-xL: 0.12 μM) containing medium. After 12 h incubation, cells were washed twice with PBS and further cultured for 48 h. Then, 10 μL of CCK-8 solution from Cell Counting Kit-8 (Dojindo Molecular Technologies, CK04) was added to each well and incubated for 3 h. The absorbance of the solution was measured at 450 nm using a plate reader (Tecan, Mannedorf, Switzerland).

Animal Studies and Histologic Analysis

N134-RHAMM$^B$ cells ($5 \times 10^6$) were subcutaneously injected into RIP-TVA mice (C57BL6 background) on one side of the flank. When tumors reached 4 mm$^3$, either Au/L/HA (template particles, 150 μL, 10 nmol) or Au/L/siB/K/HA (therapeutic particles, 150 μL; siBcl-xL: 0.67 mg/kg, KLA: 2.84 mg/kg) were injected via tail vein, twice weekly. Tumor size was measured using a caliper, and tumor volume (mm$^3$) was calculated using a standard formula (W$^2$×L)/2×1000, where L is the long diameter and W is the short diameter. Tumors and main organs were harvested for fluorescence imaging using an IVIS Spectrum imaging system (Perkinelmer, Waltham, MA) with excitation at 640 nm and emission at 700 nm.

For histologic analysis, the excised tumor samples and the organs of interest, including lung and heart, liver, kidneys, spleen and pancreas, were fixed in 10% formalin overnight and stored in 70% ethanol. Subsequently, tissues and tumors were embedded in paraffin, and 5 μm sections were prepared and stained with Hematoxylin and eosin Y solution (H&E) for histologic evaluation via light microscopy. Immunohistochemical staining (IHC) of proliferation index was performed using Ki67 (Abcam, ab16667) antibody on paraffin embedded mouse tissue sections on a Leica Bond system (Buffalo Grove, IL) using the modified protocol F provided by the manufacturer. The section was pre-treated using heat mediated antigen retrieval with Tris-EDTA buffer (pH=9, epitope retrieval solution 2) and incubated with the antibody (dilution 1:100) for overnight at room temperature. Signal was detected using an HRP conjugated compact polymer system and DAB as the chromogen. Each section was counterstained with haematoxylin and mounted with Leica Micromount. Immunohistochemical detection of activated caspase-3, a sensitive and reliable method for detecting and quantifying apoptosis, was similarly performed using cleaved caspase 3 antibody (Cell Signaling, 9664, 1:1,000).

Immune Cell Profiling

The following antibodies and reagents were used for flow cytometry: CD16/32, CD45-APC (clone 30-F11), CD3-APC/Cy7 (clone 17A2), CD4-PE/Cy7 (clone GK1.5), CD8-PE (clone 53-6.7), B220-FITC (clone RA3-6B2), CD11b-FITC (clone M1/70), Ly6G-PE (clone 1A8), Ly6C-PE/Cy7 (clone HK1.4), CD11c-PE/Cy7 (clone N418), MHCll-APC/Cy7 (clone M5/114.15.2) and Live/Dead Zombie UV™ Fixable viability kit were purchased from Biolegend. All antibodies were tested with their isotype controls. Primary tumor tissues were harvested, weighed and digested with tissue dissociation buffer (~280 U/mL Collagenase Type III, 4 μg/mL DNase in HBSS) for 1 h in 37° C. water bath with periodic vortexing and then mashed through 70 m filters to get single cell suspension. After 20 min incubation with Zombie UV™ Fixable stain at room temperature, all samples were washed with BD FACS buffer and stained with the appropriate surface antibodies. Data acquisition was performed on FACSCabibur (BC Biosciences) and analyzed via FlowJo.

Statistical Analysis

Each experiment was repeated independently at least three times. Unless otherwise noted, data are presented as mean and SEM. Student's t-test was used to compare two groups of independent samples. One-way ANOVA was used to test differences among three groups, followed by post hoc comparison with Dunnett test to adjust p values for multiple pairwise comparisons.

To compare the overall difference of tumour growth over time, tumor size was transformed to nature log scale before analysis and a GEE method was used to test the significance of difference. All statistical comparisons were two-sided with an alpha level of 0.05 as the significance cutoff. Analyses were performed in statistical software SAS Version 9.4 (SAS Institute, Cary, NC).

Figure 1A:
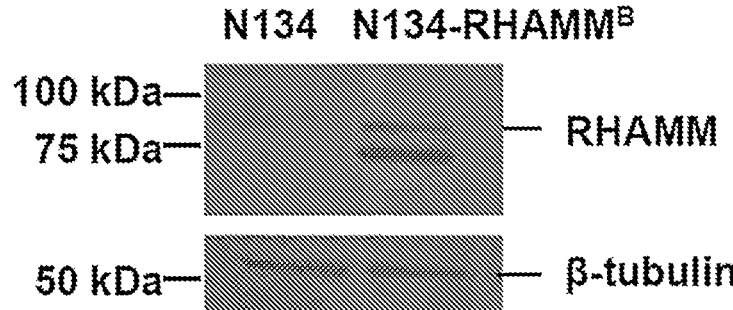
FIGS. 1A-1E illustrate that RHAMM[B] is crucial for liver metastasis of PNET cells and mediates cellular uptake of RHAMM[B]-targeting HA-coated NPs (Au/L/HA).
Figure 1B:
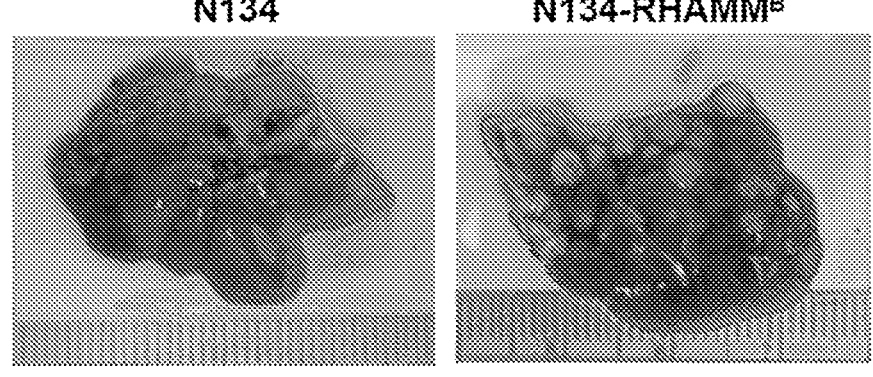

RHAMM$^B$ is Crucial in PNETs and Mediates Cellular Uptake of HA-Coated AuNPs in PNET Cells To validate the critical role of human RHAMM$^B$ in metastatic progression of PNETs [18], a new batch of mouse PNET N134 cells expressing human RHAMM$^B$ was generated. The expression of human RHAMM$^B$ (~82 kDa) was verified in the new N134-RHAMM$^B$ cell line by Western blotting using an antibody specific against human RHAMM (FIG. 1A). An additional lower molecular weight band was detected only in N134-RHAMM$^B$ cells, likely representing a degradation product of RHAMM protein. To confirm the metastatic function of RHAMM$^B$ in vivo, 2×10$^6$ N134 or N134-RHAMM$^B$ cells were injected into immunodeficient NOD/scid-IL2Rgc knockout (NSG) mice via tail vein (n=5). Six weeks later, the recipient mice were euthanized. None of the mice receiving N134 cells developed liver metastases and all 5 mice receiving N134-RHAMM$^B$ cells developed large liver metastases (FIG. 1B), supporting the metastatic function of human RHAMM$^B$.

Figure 1C:
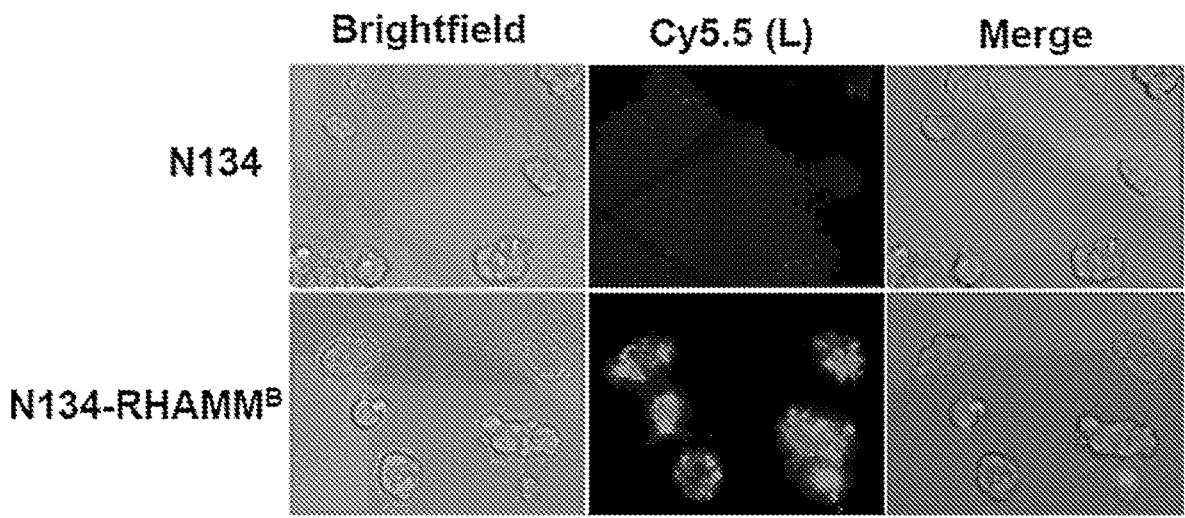
Figure 1D:
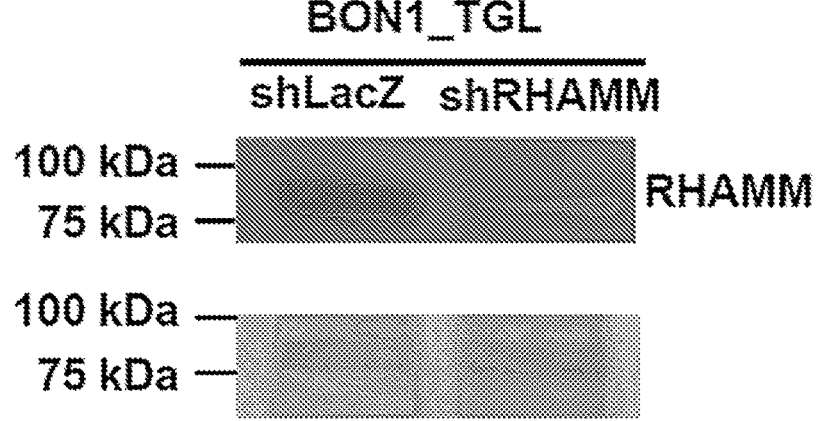
Figure 1E:
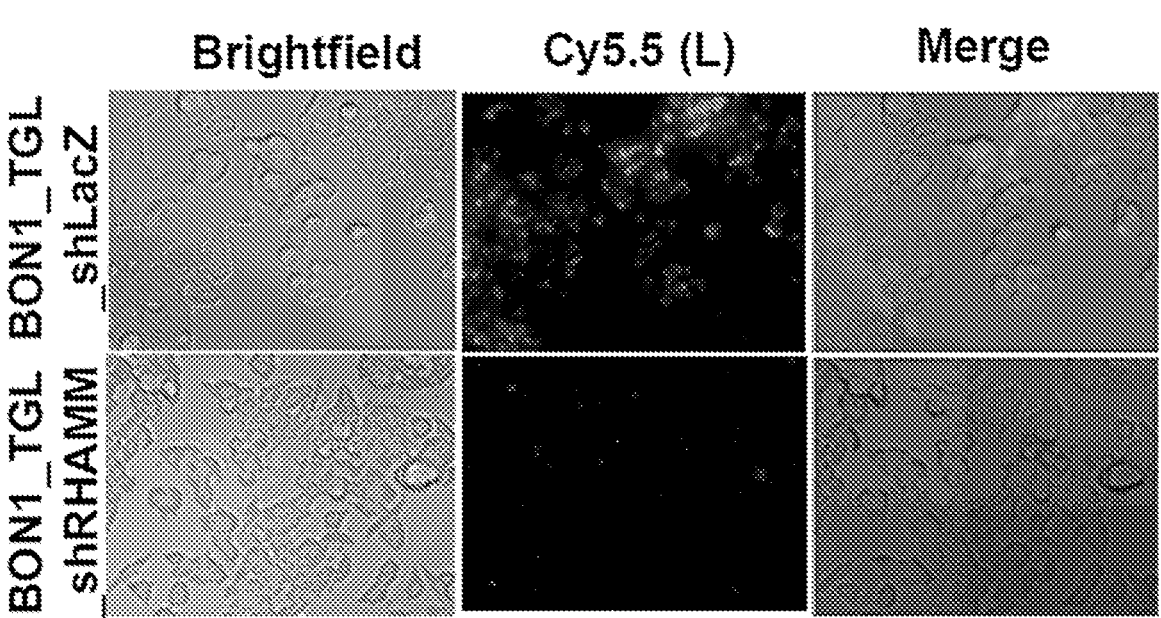

RHAMM is a receptor of hyaluronic acid (HA). To investigate the potential of HA-coated AuNPs to specifically target human RHAMM$^B$-expressing mouse PNET cells, Au/L/HA NPs (Table 1) were prepared. AuNPs was first layered by positively charged Poly-L-Lysine (PLL) and then coated with negatively charged HA on the surface of NPs. For tracking purpose, PLL were labeled by Cy5.5. Au/L/HA NPs were added into the culture medium of N134 and N1344-RHAMM$^B$ cells. 12 h later, strong intracellular Cy5.5 fluorescence signal in N134-RHAMM$^B$ cells, but no signals in N134 cells, was observed, indicating that HA-coated AuNPs were selectively picked up by RHAMM$^B$-expressing PNET cells (FIG. 1C). To further verify the RHAMM$^B$-dependent HA-coated AuNPs uptake, a previously generated human PNET cell line with reduced level of RHAMM by shRNA knockdown (BON1_TGL_shRHAMM) and a control cell line, BON1_TGL_shLacZ [18], were used (FIG. 1D). BON1 cells upregulate RHAMM, especially RHAMM$^B$ isoform, compared to normal human islets [18]. BON1_TGL_shLacZ and BON1_TGL_shRHAMM cells were incubated with Au/L/HA NPs for 12 h and then the cells were imaged under fluorescence microscope. BON1_TGL_shRHAMM cells showed significantly decreased cellular uptake of HA-coated AuNPs comparing with BON1_TGL_shLacZ cells (FIG. 1E).

Figure 7:
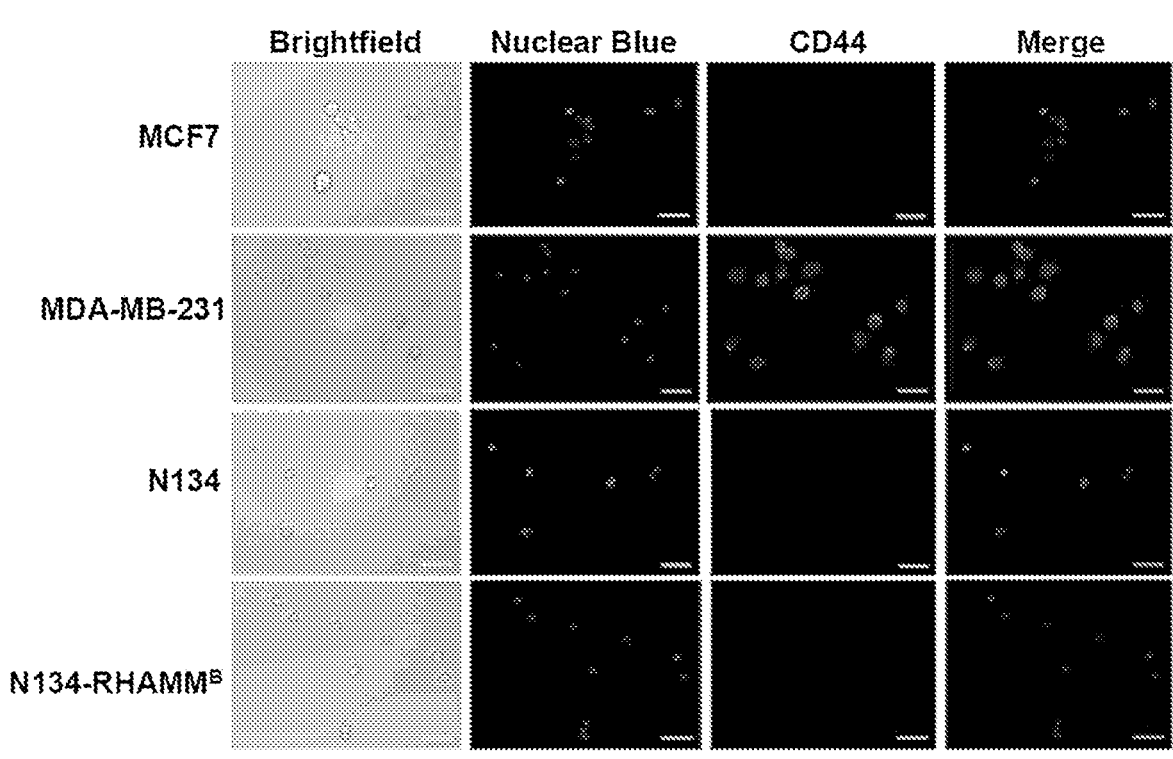
FIG. 7 illustrates CD44 expression on the surface of N134 and N134-RHAMM$^B$ cells. Cells were seed in 96-well black clear-bottom culture plate at a density of 5,000 cells per well and incubated for 48 h. CD44 was detected using AlexaFluor 488 conjugated anti-CD44 antibody. Nuclei were stained with NucBlue Live Cell Stain ReadyProbes reagent. Fluorescence images were acquired using a Lionheart FX Automated Microscope (magnification ×20). Two human breast cancer cell lines, MCF7 (CD44⁻) and MDA-MB-231 (CD44⁺), were used as controls for CD44 expression.

RHAMM and Cluster of Differentiation 44 (CD44) are two major receptors of HA [29]. To address whether CD44 may also facilitate the uptake of HA-coated AuNPs in N134-RHAMM$^B$ cells, the CD44 expression levels in N134 and N134-RHAMM$^B$ cells were determined. CD44 on the surface of N134 and N134-RHAMM$^B$ cells was stained using AlexaFluor 488 conjugated anti-CD44 antibody followed by live cell imaging. It was found that CD44 was not detectable on the cell surface of both N134 and N134-RHAMM$^B$ cells (FIG. 7). MCF7 cell line, which had low CD44 expression, and MDA-MB-231 cell line with high endogenous CD44 expression were used as negative and positive controls [30] (FIG. 7). Taken together, the expression of RHAMM$^B$ without CD44 on the cell surface was sufficient for the cellular uptake of HA-coated AuNPs by RHAMM$^B$-expressing PNET cells.

Figure 2A:
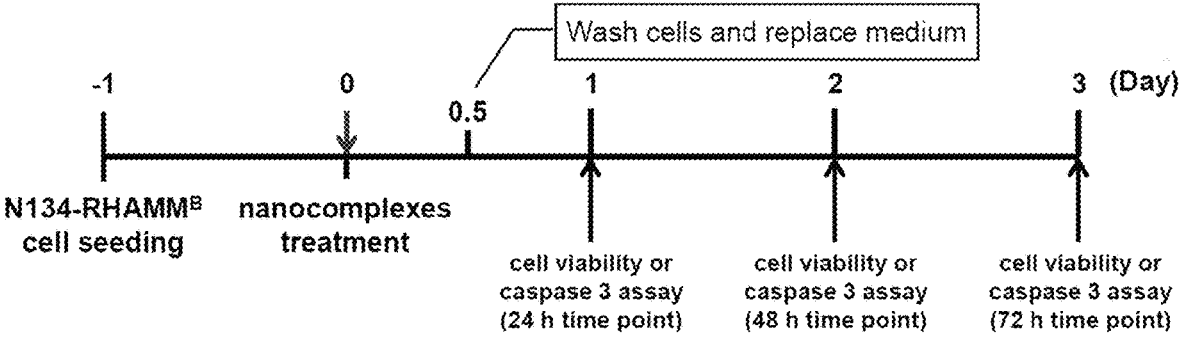
FIGS. 2A-2D illustrate the functional efficacy of the HA-coated AuNPs carrying siBcl-xL (Au/L/siB/L/HA).
Figure 2B:
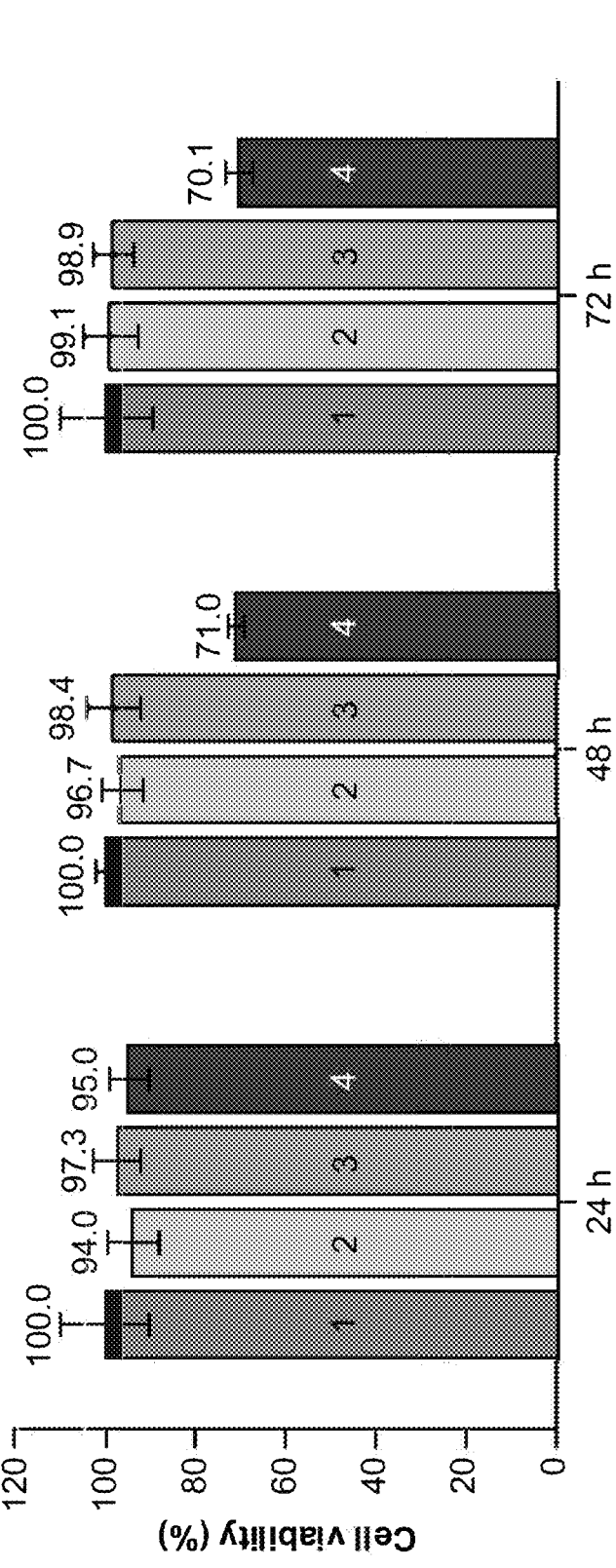
Figure 2C:
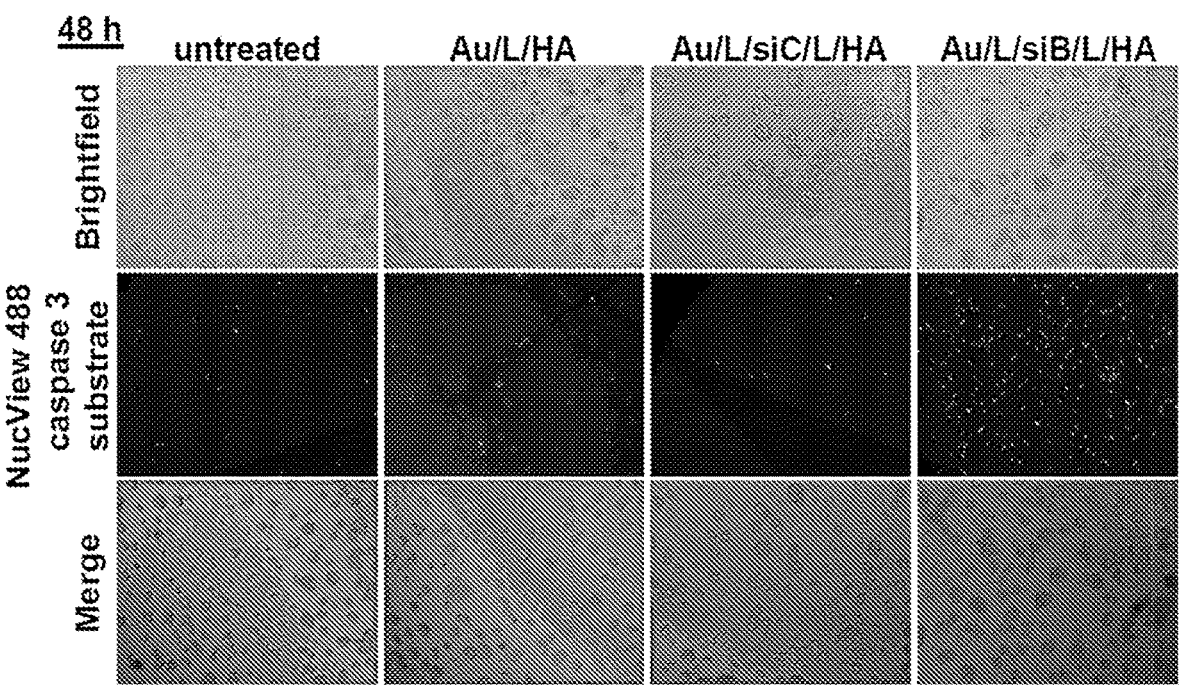
Figure 2D:
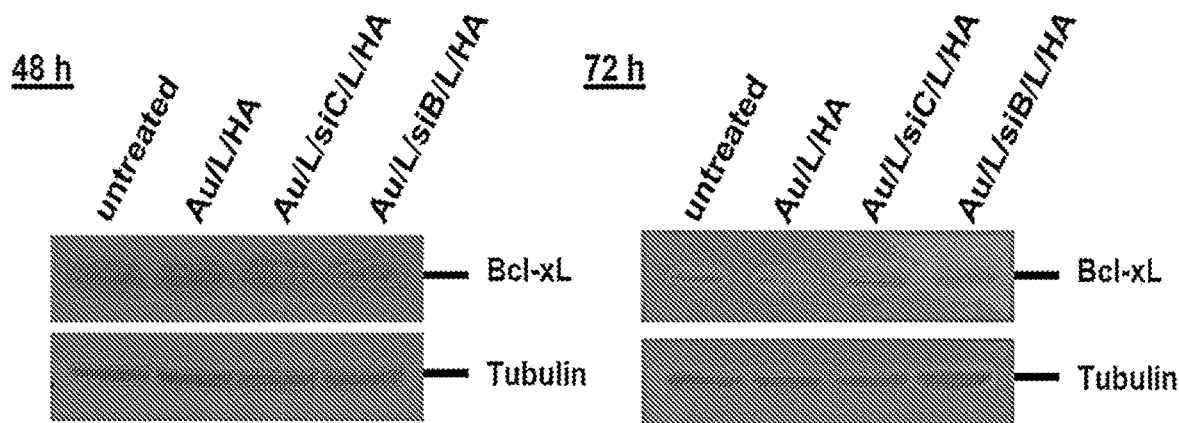
Figure 8:
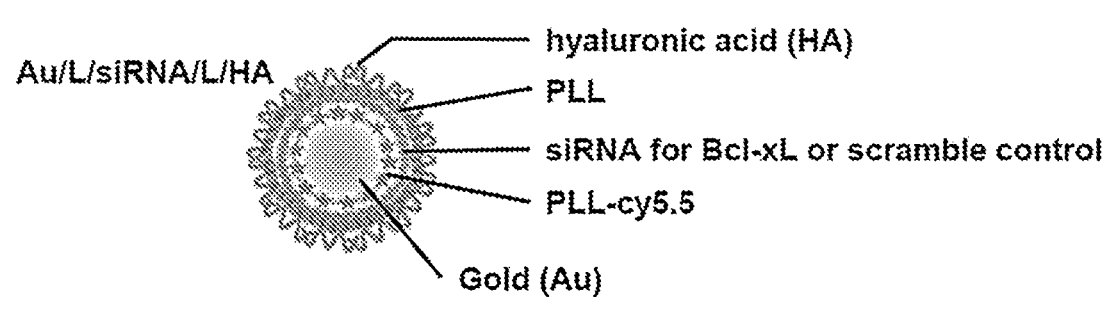
FIG. 8 provides schematic illustration of the process to prepare RHAMM$^B$-targeting siRNA nanocomplex (Au/L/siR/K/HA) by electrostatic interaction. The negatively charged AuNP core sequentially layered with PLL-Cy5.5 (+), siBcl-xL or siControl (−), KLA (+), and HA (−) using charge-charge interactions. Alternatively, RHAMM$^B$-targeting Au/K/siRNA/L/HA nanocomplexes may also be prepared.
Figure 8:
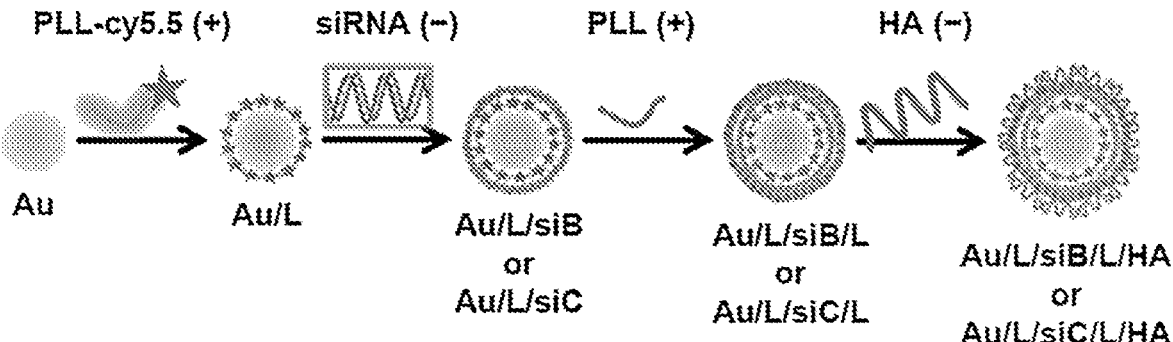
Figure 9A:
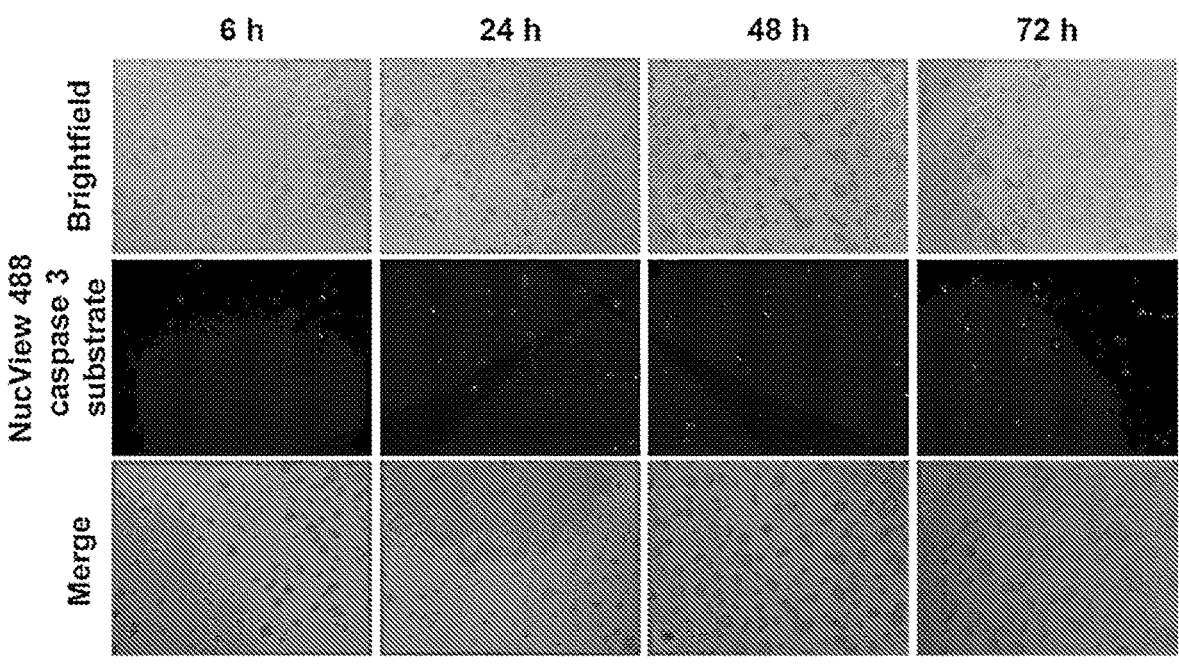
FIGS. 9A-9D illustrates caspase 3 detection in RHAMM$^B$-targeting siRNA nanocomplex treated N134-RHAMM$^B$ cells. Cells were seeded on μ-Plate 96 Well Black and cultured for 1 day, and then treated with various nanocomplex (siControl or siBcl-xL: 0.12 μM), including Au/L/HA (FIG. 9B), Au/L/siC/L/HA (FIG. 9C), Au/L/siB/L/HA (FIG. 9D), or without NPs (FIG. 9A) for 12 h. After designated time periods (24 h, 48 h, and 72 h after treatment with each nanocomplexes), the NucView 488 caspase 3 substrate (5 μM) were added and the activity of caspase 3 based on the cleaved NucView 488 caspase 3 substrate was visualized by an EVOS FL Auto Cell Imaging System using GFP filter (Ex/Em: 485/515 nm).
Figure 9B:
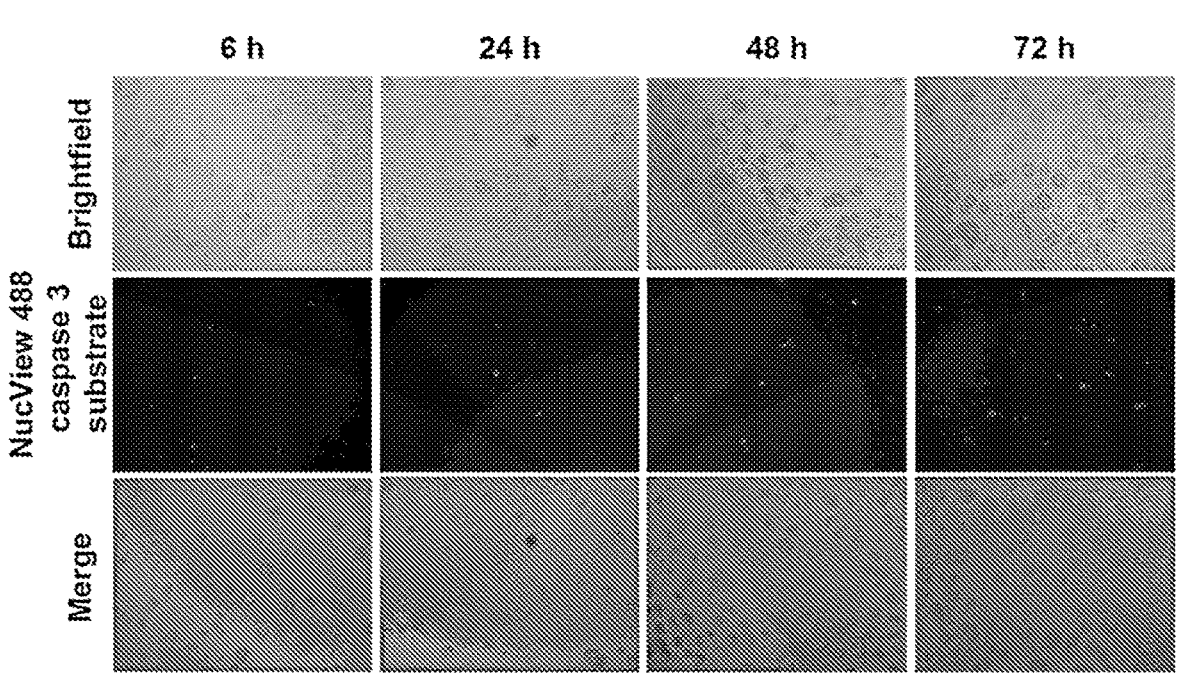
Figure 9C:
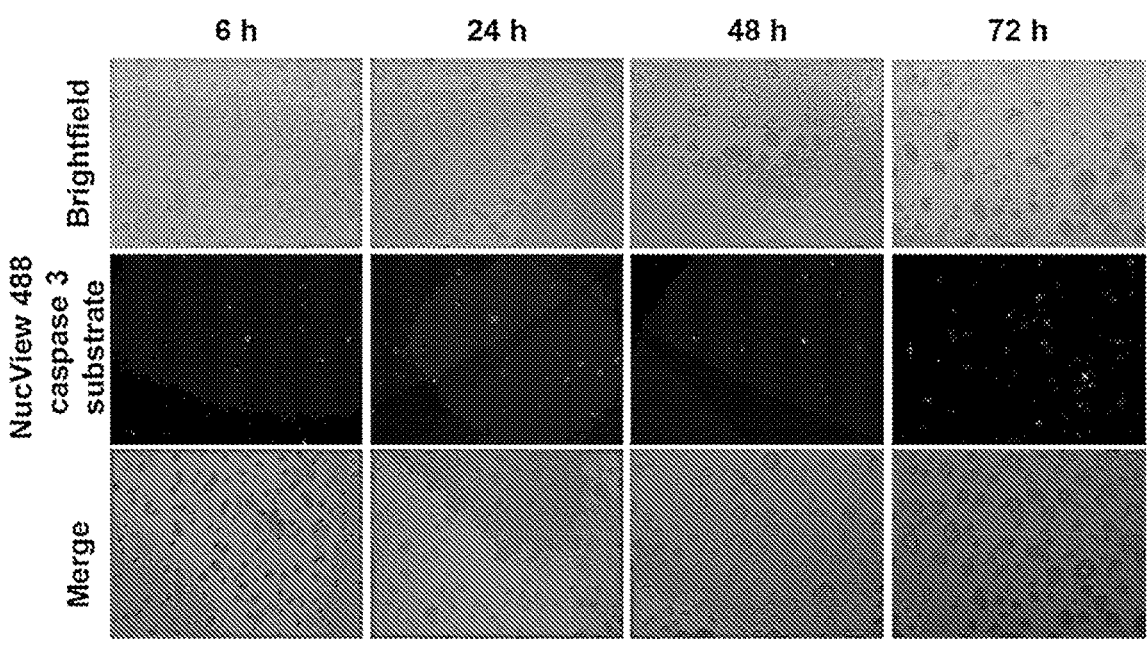
Figure 9D:
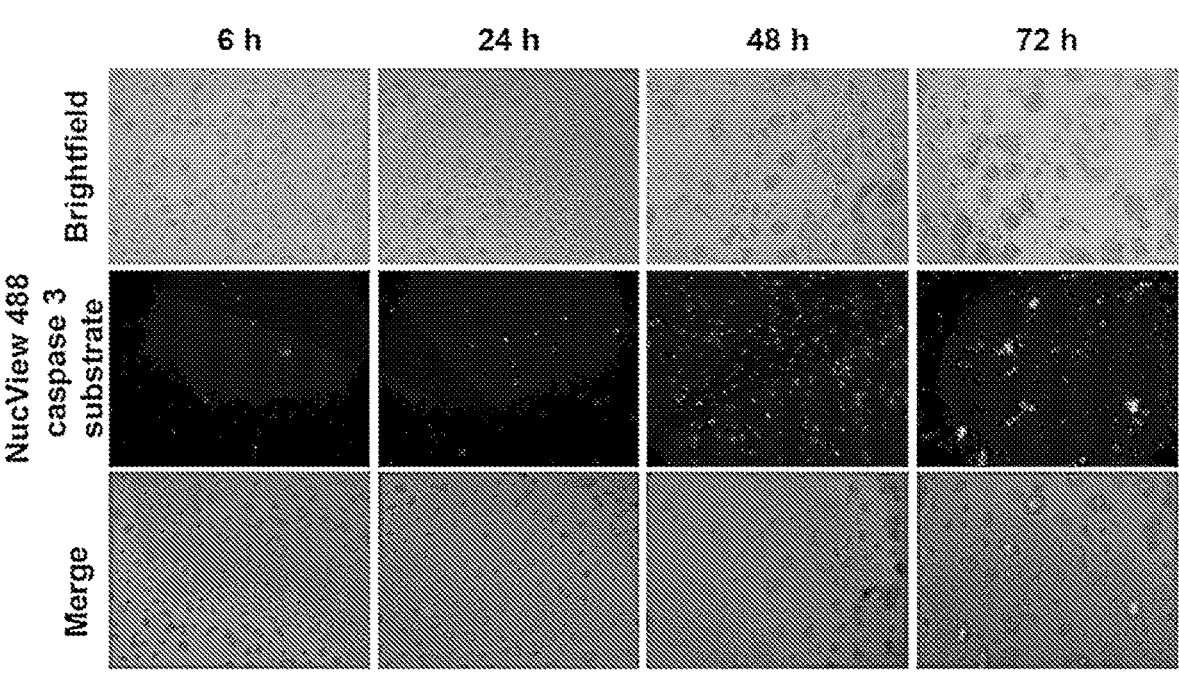

Development of RHAMM$^B$-Targeting Nanotherapy Carrying siRNA Against Bcl-xL (siBcl-xL) and KLA Peptide It was previously demonstrated that Bcl-xL promoted PNET metastasis independent of its anti-apoptosis function [15]. The dual functions of Bcl-xL in anti-apoptosis and metastasis make it an attractive therapeutic target in metastatic PNETs. The layer-by-layer fabrication strategy [23] was utilized to assemble siBcl-xL inside the HA-coated AuNPs (Table 1). The negatively charged AuNP core was sequentially layered with PLL-Cy5.5 (+), siBcl-xL (−), PLL (+), and HA (−) using charge-charge interactions (FIG. 8). (Alternatively, RHAMM$^B$-targeting Au/K/siRNA/L/HA nanocomplexes may also be prepared via a similar protocol, as further described in Lee S K, Law B, Tung C H: Versatile Nanodelivery Platform to Maximize siRNA Combination Therapy. *Macromol Biosci* 2017, 17:1600294). To determine the functional efficacy of the HA-coated AuNPs carrying siBcl-xL (siB), N134-RHAMM$^B$ cells were incubated with Au/L/HA, Au/L/scramble control siRNA (siC)/L/HA, Au/L/siBcl-xL(siB)/L/HA in the cell culture medium for 12 h. Then, NP-containing medium was replaced with regular medium (FIG. 2A). Cell viability of N134-RHAMM$^B$ cells incubated with Au/L/siB/HA was notably reduced at 48 h and 72 h (FIG. 2B). Detection of activated caspase-3 offers an easy, sensitive, and reliable method for detecting and quantifying apoptosis. Strong caspase 3 activity in N134-RHAMM$^B$ cells incubated with Au/L/siB/L/HA was also observed at 48 h and 72 h, but not in untreated cells or cells treated with Au/L/HA and Au/L/siC/L/HA (FIG. 2C and FIGS. 9A-9D). The reduction of Bcl-xL protein levels was observed at 72 h in N134-RHAMM$^B$ cells incubated with Au/L/siBcl-xL/HA, but not in untreated cells or cells treated with Au/L/HA and Au/L/siControl/L/HA (FIG. 2D). This indicated that siBcl-xL in the HA-coated AuNP knocked down Bcl-xL expression. Surprisingly, the reduction of Bcl-xL protein levels was not obvious at 48 h in N134-RHAMM$^B$ cells incubated with Au/L/siBcl-xL/HA (FIG. 2D), when caspase 3 activity was elevated and ~30% of cells lost their viability (FIG. 2B and FIG. 2C). The data indicated that siBcl-xL has a novel way to induce cell death before downregulating Bcl-xL protein expression.

Figure 3A:
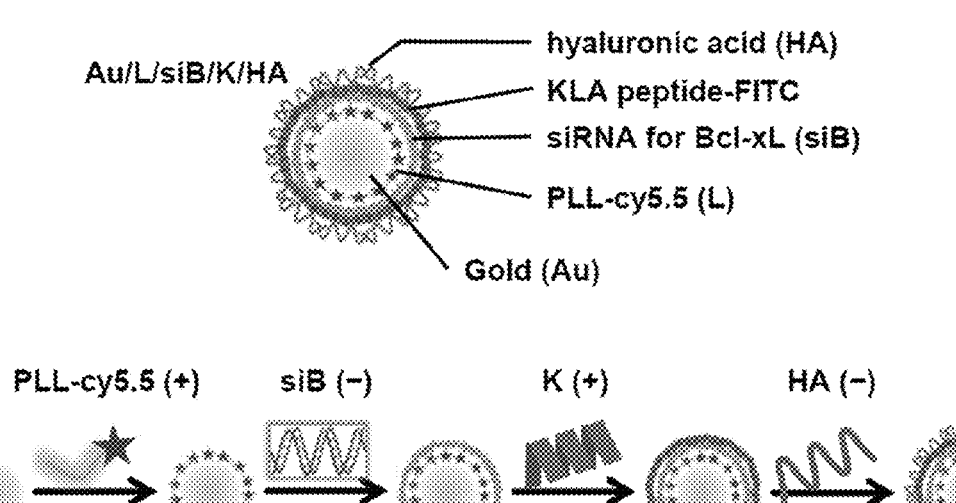
FIGS. 3A-3B provide characterization of the RHAMM$^B$-targeting combinational nanocomplex, Au/L/siB/K/HA.
Figure 3B:
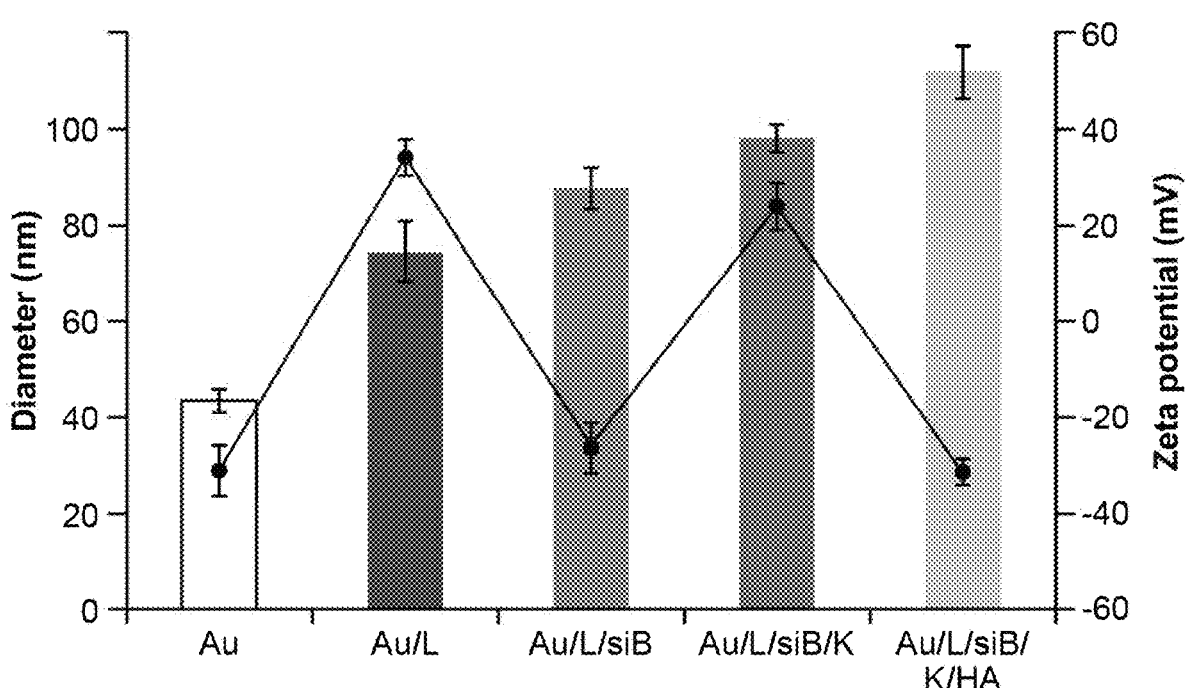

To increase the cytotoxicity of the HA-coated AuNPs, siBcl-xL was co-delivered with a KLA mitochondria-fusing peptide. KLA is an amphipathic antimicrobial peptide [8]. Although KLA can disrupt bacterial cell membrane, it cannot penetrate eukaryotic plasma membrane. However, once inside eukaryotic cells, it can disrupt the mitochondrial membrane and cause apoptosis [31]. It is hypothesized that the co-delivery of siBcl-xL and KLA peptide will synergize to drive apoptosis. To generate RHAMM$^B$-targeting AuNPs co-delivering siBcl-xL and KLA peptides, the negatively charged AuNP core was sequentially layered with PLL-Cy5.5 (+), siBcl-xL (−), KLA-FITC (+), and HA (−) using charge-charge interactions (FIG. 3A). To track the nanocomplexes in vitro and in vivo, the Cy5.5 and FITC fluorescence was conjugated to PLL and KLA, respectively. For the characterization of RHAMM$^B$-targeting nanocomplexes, the size of the nanocomplexes was measured by dynamic light scattering after each layer of coating. As shown in FIG. 3B, the size of the initial bare AuNP was 40 nm and its size increased steadily with the number of layers added. Au/L: 75 nm; Au/L/siBcl-xL (Au/L/siB): 88 nm; Au/L/siBcl-xL/KLA (Au/L/siB/K): 98 nm; Au/L/siBcl-xL/KLA/HA (Au/L/siB/K/HA): 112 nm. Based on the charge-charge interactions, the zeta potentials of fabricated particle after coating stands for the surface charge of each polymer (FIG. 3B). The initial zeta potential of bare AuNPs was −31 mV. The PLL coating brought the surface charge up to about +34 mV. The subsequent siRNA layer dragged it down to about −26 mV and the KLA layer converted it to +24 mV. The final surface charge of the assembled Au/L/siB/K/HA was about −30 mV. The zigzag pattern of the surface zeta potential demonstrated the successful coating of each layer (FIG. 3B).

Figure 4A:
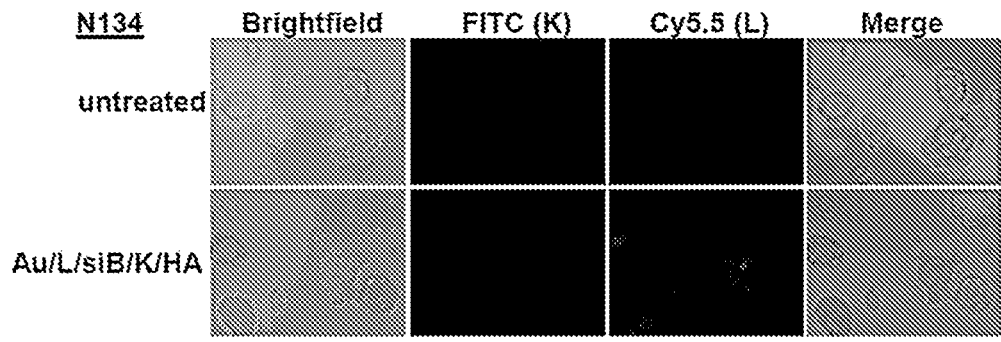
FIGS. 4A-4C illustrate in vitro functional efficacy of the RHAMM$^B$-targeting combinational nanocomplexes. Images of nanocomplexes uptake in N134 (FIG. 4A) and N134-RHAMM$^B$ (FIG. 4B) cells (magnification: ×40). Cells were seeded on 96-well plate. After one day, cells were treated with Au/L/siB/K/HA or different nanocomplex controls for 12 h and washed twice with PBS. Cells were then incubated in complete medium for additional 48 h and visualized using fluorescence microscopy. Untreated N134 and N134-RHAMM$^B$ were used as control.
Figure 4B:
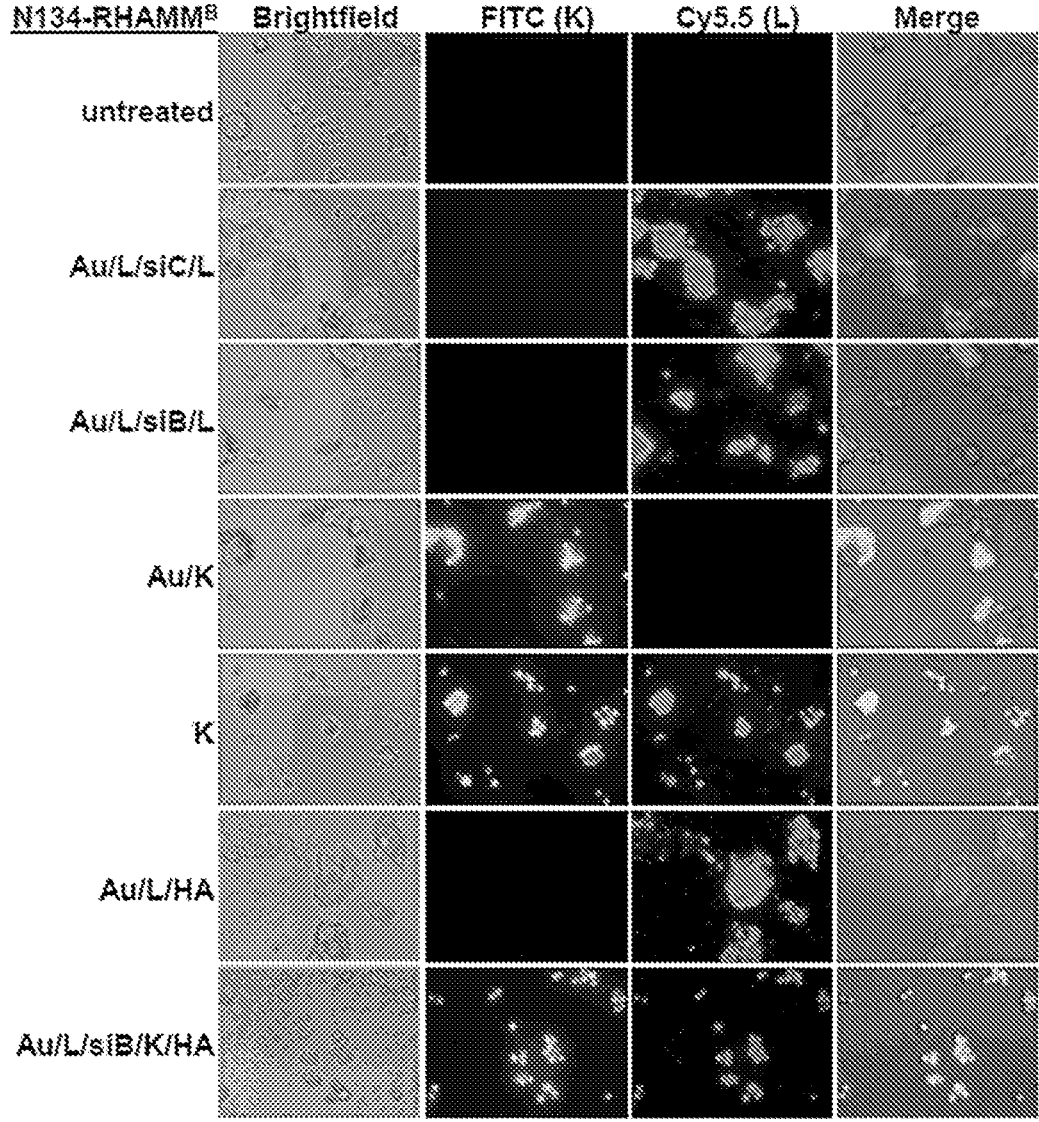
Figure 4C:
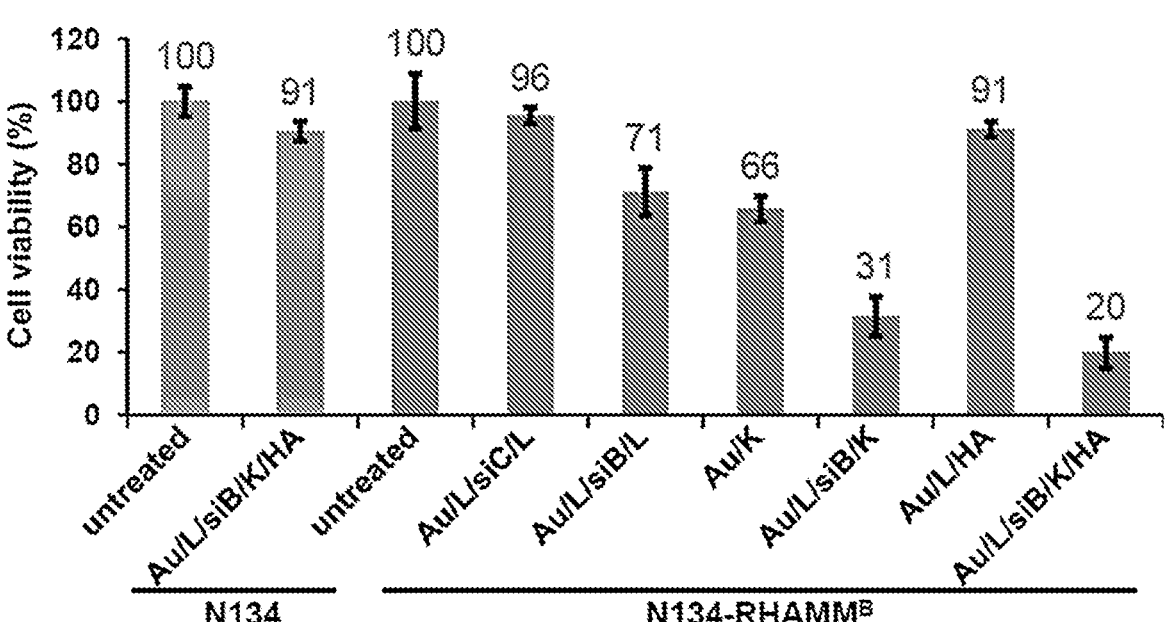

To examine cellular uptake and cytotoxicity of nanocomplexes, N134 or N134-RHAMM$^B$ cells were treated with various NPs including Au/L/siC/L, Au/L/siB/L, Au/K, Au/L/siB/K, Au/L/HA, and Au/L/siB/K/HA for 12 h. After additional culture for 48 h, the internalization of FITC-conjugated KLA peptide and Cy5.5-conjugated PLL was examined under a fluorescent microscope. The untreated N134 and N134-RHAMM$^B$ cells were used as controls. As expected, the negatively charged Au/L/siB/K/HA could not be internalized by N134 cell. No fluorescent signal were detected due to the lack of HA-RHAMM binding in RHAMM$^B$-negative N134 cells (FIG. 4A). 91% cells remained viable in N134 cells treated with Au/L/siB/K/HA NPs (FIG. 4C). On the other hand, both positively charged NPs, including Au/L/siC/L, Au/L/siB/L, Au/K, Au/L/siB/K, and HA-coated negatively charged NP, including Au/L/HA, and Au/L/siB/K/HA were internalized by N134-RHAMM$^B$ cells (FIG. 4B). It indicated that the positively charged particles, which have PLL or KLA as the surface layer, non-specifically entered cells, while the negatively charged particles, which have HA as the surface layer, only entered the N134-RHAMM$^B$ cells thought RHAMM$^B$.

In N134-RHAMM$^B$ cells, AuNPs carrying with either siBcl-xL or the KLA peptide alone showed only moderate cell toxicity (71% or 66% viable, respectively). In contrast, siBcl-xL and the KLA peptide combined Au/L/siB/K NPs had a significant cell killing effect (31% viable), evidencing the synergistic therapeutic effect from siBcl-xL and the KLA peptide (FIG. 4C). Furthermore, RHAMM$^B$-targeting co-delivery of siBcl-xL and the KLA peptide (Au/L/siB/K/HA) led to lowest cell viability (20%, FIG. 4C).

Au/L/siB/K/HA NPs Inhibits Tumor Growth in a Syngeneic Mouse Model

Figure 5A:
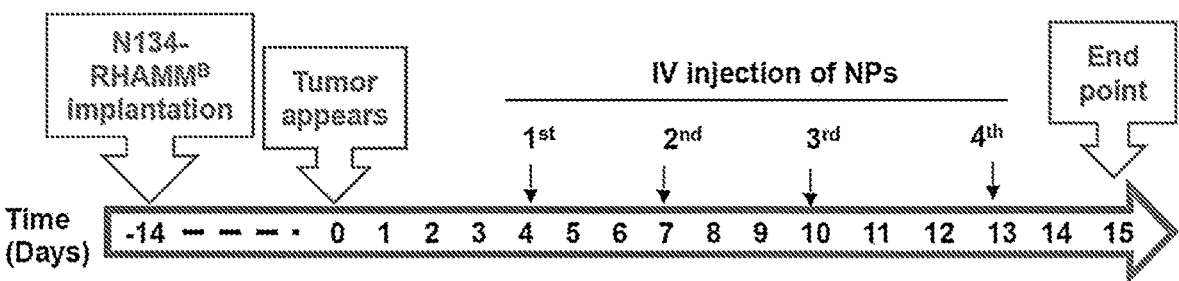
FIGS. 5A-5D illustrate in vivo therapeutic efficacy and biodistribution of the RHAMM$^B$-targeting combinational nanocomplexes.
Figure 5B:
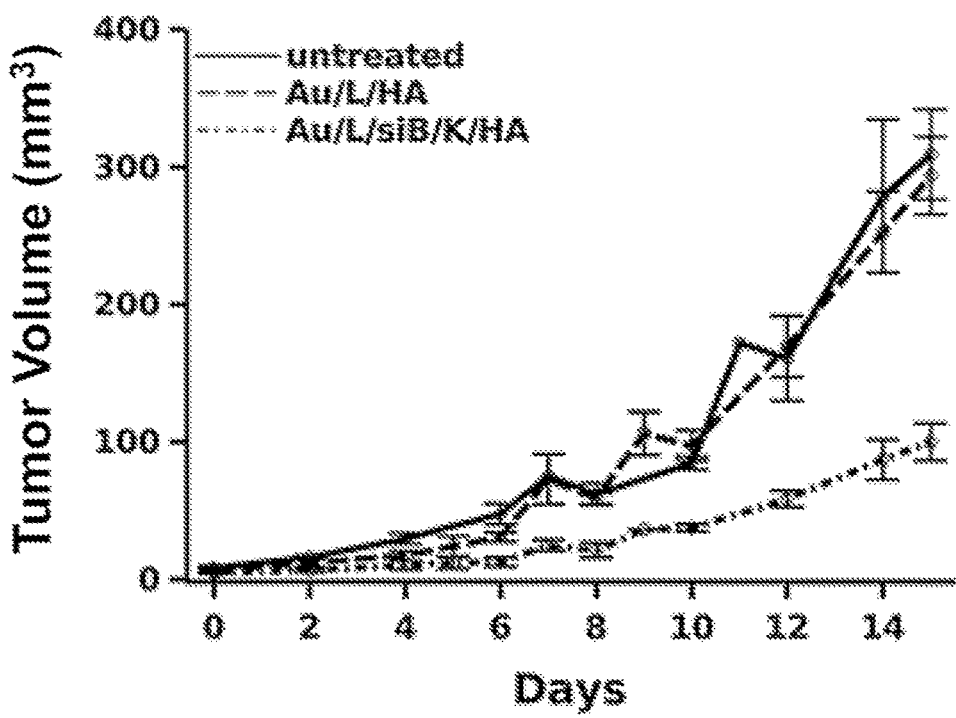
Figure 5C:
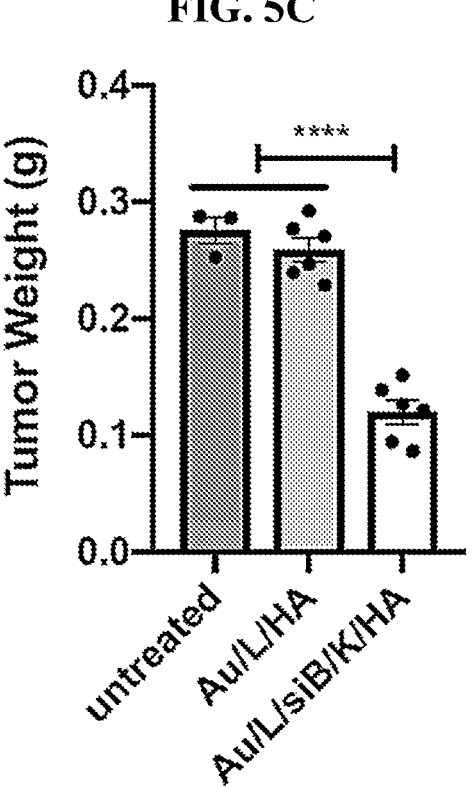

To investigate the anti-cancer effect of RHAMM$^B$-targeting co-delivery of siBcl-xL and KLA peptide (Au/L/siB/K/HA) in vivo, a subcutaneous tumor model using syngeneic mice was employed. N134-RHAMM$^B$ cells were subcutaneously inoculated to RIP-TVA syngeneic mice. After tumor burden reaches 4 mm$^3$, the mice were randomly divided into 3 treatment groups (n≥3 per group) (i) untreated, (ii) Au/L/HA control NP, and (iii) Au/L/siB/K/HA NP. The NPs were injected via tail vein twice weekly for two weeks (FIG. 5A). The tumor growth rates were similar between untreated control and Au/L/HA treatment (FIG. 5B, GEE method: P=0.253). On the other hand, the difference in the growth rate between the Au/L/siB/K/HA treated tumors and Au/L/HA treated tumors was significant (FIG. 5B). Tumor size in the Au/L/siB/K/HA treated mice decreased 0.059 per day (in log scale) compared to that in the Au/L/HA treated mice (GEE method: P=0.0001), evidencing that Au/L/siB/K/HA treatment dramatically inhibited tumor growth. After two weeks of treatment, mice were euthanized to harvest tumors and major organs. Tumor weight in (iii) Au/L/siB/K/HA NP group was significantly lighter (~35%, P<0.0001) than that in (i) untreated control and (ii) Au/L/HA control NP groups (FIG. 5C).

To trace the biodistribution of the NPs, Cy5.5 was conjugated with PLL inside the NPs. The Cy5.5 signal of tumors and the major organs was measured via ex vivo imaging at the end point (FIG. 5A). Only the tumors from the two NP treated groups presented intense fluorescence of Cy5.5 signal, but not the tumors from the untreated group (FIG. 5D, upper middle wells in each 6-well plate), evidencing that IV injected HA-coated AuNPs were successfully delivered into RHAMM$^B$-positive tumors in vivo. While about 4-9% of 27 28

Figure 5D:
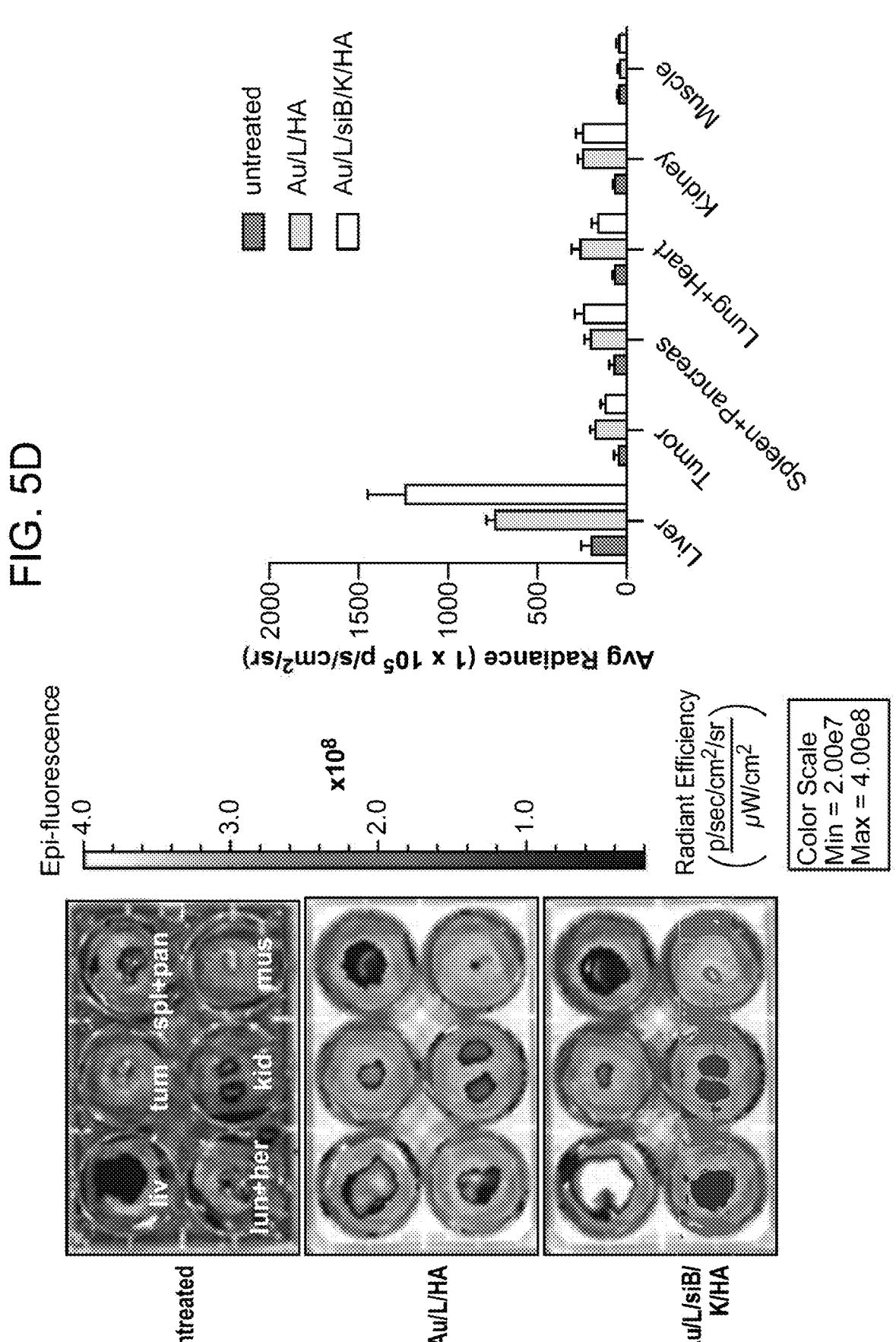

Cy5.5 signals were located to the tumors at this time point, the majority of Cy5.5 signals were found in the liver (FIG. 5D).

To examine whether the Au/L/siB/K/HA treatment elicited immune responses in the syngeneic mice to suppress tumor growth, the whole tumors were harvested 2 days after the $4^{th}$ NP treatment and digested into single cells for immune cell profiling by flow cytometry. Cells were stained for surface CD45, CD3, CD8, CD4, B220, MHCII, Ly6G, and Ly6C. No significant difference in CD45$^+$ cells, CD8$^+$ T cells, CD4$^+$ T cells, B cells, dendric cells, or myeloid-derived suppressor cells (MDSC) between the Au/L/HA control NP verse Au/L/siB/K/HA group was observed (FIGS. 10A-10F). The data evidences that the suppression of tumor growth by Au/L/siB/K/HA NP treatment was not mediated through host immune responses.

Figure 6A:
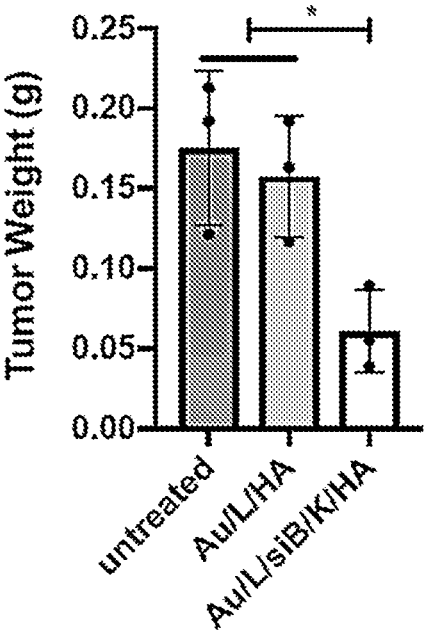
FIGS. 6A-6F illustrate anti-tumor effect and toxicity profile of the RHAMM$^B$-targeting combinational nanocomplexes.
Figures 6B, 6C, 6D, 6E, 6F:
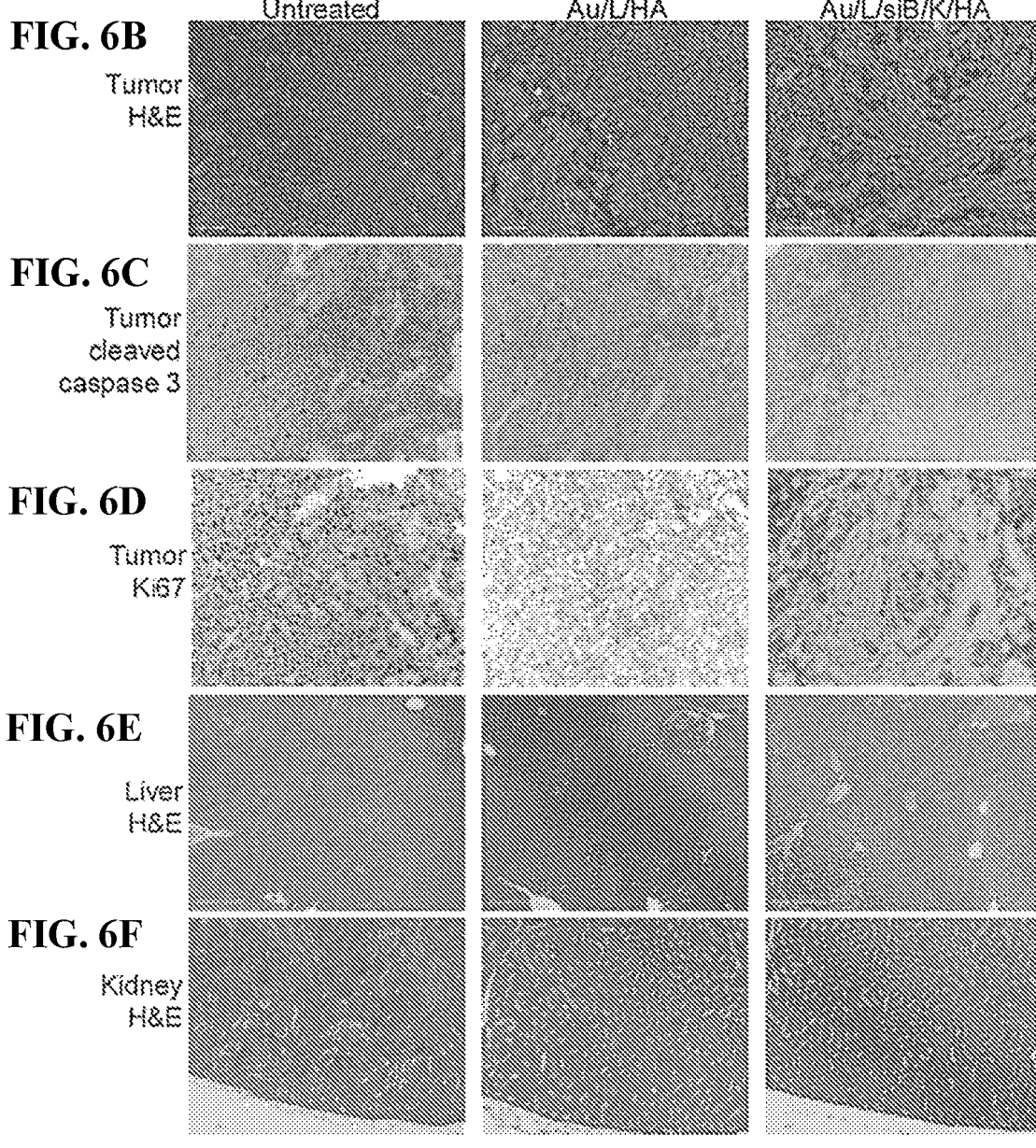

To further evaluate the inhibitory effect of Au/L/siB/K/HA on tumor growth, the tumors were analyzed after 1 week of NP treatment. N134-RHAMM$^B$ cells were subcutaneously inoculated to RIP-TVA mice. After tumor burden reaches 4 mm$^3$, the mice were randomly divided into 3 treatment groups including (i) untreated, (ii) Au/L/HA control NP, and (iii) Au/L/siB/K/HA NP. NPs were injected via tail vein twice weekly for 1 week. Similar to the 2-week time point in FIG. 5C, tumors in (iii) Au/L/siB/K/HA NP group were smaller than that in (i) untreated and (ii) Au/L/HA control NP groups (FIG. 6A). Histologic analysis revealed that tumors treated with Au/L/siB/K/HA contained more fibrous stroma and were lower in tumor cellularity than untreated and Au/L/HA tumors (FIG. 6B). Although scattered cleaved caspase 3-positive apoptotic cells were present in the tumors of (i) untreated and (ii) Au/L/HA control NP groups, almost no cleaved caspase 3-positive cells were found in tumors treated with Au/L/siB/K/HA, evidencing a decreased apoptosis and cell turnover in the remaining tumor cells at this stage of stromal fibrosis (FIG. 6C). More than 80% of the remaining tumor cells were Ki67-positive in all of these three groups (FIG. 6D). Together, these results (FIGS. 4 to 6) evidence that Au/L/siB/K/HA NP kills tumor cells in vivo, and effective tumor inhibition and regression could be expected after multiple cycles of this treatment.

Similar to 2 weeks of NP treatment, highest accumulation of Cy5.5 fluorescence in the liver was observed via ex vivo imaging at this time point (data not shown). Alteration of histopathological structure of tissues on H&E stained slides was investigated, and no damage in the liver, kidney, and other organs was observed (FIGS. 6E-6F, and data not shown). Taken together, RHAMM$^B$-targeting co-delivery of siBcl-xL and KLA peptide (Au/L/siB/K/HA) specifically targeted RHAMM$^B$-positive PNET cells and inhibited tumor growth when administrated systemically.

RHAMM is Overexpressed in Human Breast Cancer MDA-MB-231 Cells and Mediates Cellular Uptake of HA-Coated AuNPs in MDA-MB-231 Cells FIG. 11 illustrates that RHAMM is overexpressed in human breast cancer of The Cancer Genome Atlas (TCGA). To investigate whether HA-coated AuNPs can enter RHAMM-expressing human breast cancer MDA-MB-231 cells, AuNPs were first layered by positively charged poly-L-lysine (PLL) and then coated with negatively charged HA on the surface of NPs. For tracking purposes, PLL was labeled by covalently conjugating Cy5.5. The resulting Au/L/HA NPs were added into a culture medium of MDA-MB-231 cells. 12 h later, strong intracellular Cy5.5 fluorescence signal in treated MDA-MB-231 cells, but no signals in untreated MDA-MB-231 cells, were observed, evidenc-ing that HA-coated AuNPs enter RHAMM-expressing MDA-MB-231 cells (FIG. 12).

REFERENCES

1. Franko J, Feng W, Yip L, Genovese E, Moser A J: Non-functional neuroendocrine carcinoma of the pancreas: incidence, tumor biology, and outcomes in 2,158 patients. *J Gastrointest Surg* 2010, 14:541-548.
2. Yao J C, Eisner M P, Leary C, Dagohoy C, Phan A, Rashid A, Hassan M, Evans D B: Population-based study of islet cell carcinoma. *Ann Surg Oncol* 2007, 14:3492-3500.
3. Dasari A, Shen C, Halperin D, Zhao B, Zhou S, Xu Y, Shih T, Yao J C: Trends in the Incidence, Prevalence, and Survival Outcomes in Patients With Neuroendocrine Tumors in the United States. *JAMA Oncol* 2017, 3:1335-1342.
4. Edge S, Byrd, D. R., Compton, C. C., Fritz, A. G., Greene, F. L., Trotti, A.: Exocrine and endocrine pancreas. In *AJCC Cancer Staging Manual*. 7 edition: Springer; 2010: 241-249
5. Zhang J, Francois R, Iyer R, Seshadri M, Zajac-Kaye M, Hochwald S N: Current understanding of the molecular biology of pancreatic neuroendocrine tumors. *J Natl Cancer Inst* 2013, 105:1005-1017.
6. Blumenthal G M, Cortazar P, Zhang J J, Tang S, Sridhara R, Murgo A, Justice R, Pazdur R: FDA approval summary: sunitinib for the treatment of progressive well-differentiated locally advanced or metastatic pancreatic neuroendocrine tumors. *Oncologist* 2012, 17:1108-1113.
7. Hanahan D, Weinberg R A: Hallmarks of cancer: the next generation. *Cell* 2011, 144:646-674.
8. Ellerby H M, Arap W, Ellerby L M, Kain R, Andrusiak R, Rio G D, Krajewski S, Lombardo C R, Rao R, Ruoslahti E, et al: Anti-cancer activity of targeted pro-apoptotic peptides. *Nat Med* 1999, 5:1032-1038.
9. Inoue-Yamauchi A, Jeng P S, Kim K, Chen H C, Han S, Ganesan Y T, Ishizawa K, Jebiwott S, Dong Y, Pietanza M C, et al: Targeting the differential addiction to anti-apoptotic BCL-2 family for cancer therapy. *Nat Commun* 2017, 8:16078.
10. Al-Harbi S, Choudhary G S, Ebron J S, Hill B T, Vivekanathan N, Ting A H, Radivoyevitch T, Smith M R, Shukla G C, Almasan A: miR-377-dependent BCL-xL regulation drives chemotherapeutic resistance in B-cell lymphoid malignancies. *Mol Cancer* 2015, 14:185.
11. Ngoi N Y L, Choong C, Lee J, Bellot G, Wong A L A, Goh B C, Pervaiz S: Targeting Mitochondrial Apoptosis to Overcome Treatment Resistance in Cancer. *Cancers (Basel)* 2020, 12:574.
12. Li J Y, Li Y Y, Jin W, Yang Q, Shao Z M, Tian X S: ABT-737 reverses the acquired radioresistance of breast cancer cells by targeting Bcl-2 and Bcl-xL. *J Exp Clin Cancer Res* 2012, 31:102.
13. Mason K D, Carpinelli M R, Fletcher J I, Collinge J E, Hilton A A, Ellis S, Kelly P N, Ekert P G, Metcalf D, Roberts A W, et al: Programmed a nuclear cell death delimits platelet life span. *Cell* 2007, 128:1173-1186.
14. Croce C M, Reed J C: Finally, An Apoptosis-Targeting Therapeutic for Cancer. *Cancer Res* 2016, 76:5914-5920.
15. Choi S, Chen Z, Tang L H, Fang Y, Shin S J, Panarelli N C, Chen Y T, Li Y, Jiang X, Du Y C: Bcl-xL promotes metastasis independent of its anti-apoptotic activity. *Nat Commun* 2016, 7:10384.
16. Turley E A: Purification of a hyaluronate-binding protein fraction that modifies cell social behavior. *Biochem Biophys Res Commun* 1982, 108:1016-1024.

17. Chen Y T, Chen Z, Du Y N: Immunohistochemical analysis of RHAMM expression in normal and neoplastic human tissues: a cell cycle protein with distinctive expression in mitotic cells and testicular germ cells. *Oncotarget* 2018, 9:20941-20952.

18. Choi S, Wang D, Chen X, Tang L H, Verma A, Chen Z, Kim B J, Selesner L, Robzyk K, Zhang G, et al: Function and clinical relevance of RHAMM isoforms in pancreatic tumor progression. *Mol Cancer* 2019, 18:92.

19. Schatz-Siemers N, Chen Y T, Chen Z, Wang D, Ellenson L H, Du Y N: Expression of the Receptor for Hyaluronic Acid-Mediated Motility (RHAMM) in Endometrial Cancer is Associated With Adverse Histologic Parameters and Tumor Progression. *Appl Immunohistochem Mol Morphol* 2020, 28:453-459.

20. Wang D, Narula N, Azzopardi S, Smith R S, Nasar A, Altorki N K, Mittal V, Somwar R, Stiles B M, Du Y N: Expression of the receptor for hyaluronic acid mediated motility (RHAMM) is associated with poor prognosis and metastasis in non-small cell lung carcinoma. *Oncotarget* 2016, 7:39957-39969.

21. Ashraf S, Pelaz B, del Pino P, Carril M, Escudero A, Parak W J, Soliman M G, Zhang Q, Carrillo-Carrion C: Gold-Based Nanomaterials for Applications in Nanomedicine. *Top Curr Chem* 2016, 370:169-202.

22. Lee S K, Han M S, Tung C H: Layered nanoprobe for long-lasting fluorescent cell label. *Small* 2012, 8:3315-3320.

23. Lee S K, Law B, Tung C H: Versatile Nanodelivery Platform to Maximize siRNA Combination Therapy. *Macromol Biosci* 2017, 17:1600294.

24. Lee S K, Law B, Tung C H: Multifunctional Nanodelivery Platform for Maximizing Nucleic Acids Combination Therapy. *Methods Mol Biol* 2020, 2115:79-90.

25. Mu P, Nagahara S, Makita N, Tarumi Y, Kadomatsu K, Takei Y: Systemic delivery of siRNA specific to tumor mediated by atelocollagen: combined therapy using siRNA targeting Bcl-xL and cisplatin against prostate cancer. *Int J Cancer* 2009, 125:2978-2990.

26. Du Y C, Lewis B C, Hanahan D, Varmus H: Assessing tumor progression factors by somatic gene transfer into a mouse model: Bcl-xL promotes islet tumor cell invasion. *PLoS* biology 2007, 5:e276.

27. Du Y C, Chou C K, Klimstra D S, Varmus H: Receptor for hyaluronan-mediated motility isoform B promotes liver metastasis in a mouse model of multistep tumorigenesis and a tail vein assay for metastasis. *Proceedings of the National Academy of Sciences of the United States of America* 2011, 108:16753-16758.

28. Zhang G, Chi Y, Du Y N: Identification and Characterization of Metastatic Factors by Gene Transfer into the Novel RIP-Tag; RIP-tva Murine Model. *J Vis Exp* 2017.

29. Stern R: Hyaluronan in cancer biology. 1st edition. pp. xxvii, 426 p., 412 p. of plates. San Diego, CA: Academic Press/Elsevier; 2009:xxvii, 426 p., 412 p. of plates.

30. Hiraga T, Ito S, Nakamura H: Cancer stem-like cell marker CD44 promotes bone metastases by enhancing tumorigenicity, cell motility, and hyaluronan production. *Cancer Res* 2013, 73:4112-4122.

31. Law B, Quinti L, Choi Y, Weissleder R, Tung C H: A mitochondrial targeted fusion peptide exhibits remarkable cytotoxicity. *Mol Cancer Ther* 2006, 5:1944-1949.

32. Leon Shargel, Susanna Wu-Pong, Yu A B C: *Applied Biopharmaceutics & Pharmacokinetics*. 6 edn: McGraw-Hill Education; 2012.

33. Hamilton S R, Fard S F, Paiwand F F, Tolg C, Veiseh M, Wang C, McCarthy J B, Bissell M J, Koropatnick J, Turley E A: The hyaluronan receptors CD44 and Rhamm (CD168) form complexes with ERK1,2 that sustain high basal motility in breast cancer cells. *J Biol Chem* 2007, 282:16667-16680.

34. Misra S, Hascall V C, Markwald R R, Ghatak S: Interactions between Hyaluronan and Its Receptors (CD44, RHAMM) Regulate the Activities of Inflammation and Cancer. *Front Immunol* 2015, 6:201.

35. Wang H, Agarwal P, Zhao S, Yu J, Lu X, He X: Combined cancer therapy with hyaluronan-decorated fullerene-silica multifunctional nanoparticles to target cancer stem-like cells. *Biomaterials* 2016, 97:62-73.

36. Wang F, Li L, Liu B, Chen Z, Li C: Hyaluronic acid decorated pluronic P85 solid lipid nanoparticles as a potential carrier to overcome multidrug resistance in cervical and breast cancer. *Biomed Pharmacother* 2017, 86:595-604.

37. Jeannot V, Gauche C, Mazzaferro S, Couvet M, Vanwonterghem L, Henry M, Didier C, Vollaire J, Josserand V, Coll J L, et al: Anti-tumor efficacy of hyaluronan-based nanoparticles for the co-delivery of drugs in lung cancer. *J Control Release* 2018, 275:117-128.

38. Sohr S, Engeland K: RHAMM is differentially expressed in the cell cycle and downregulated by the tumor suppressor p53. *Cell Cycle* 2008, 7:3448-3460.

39. Daniel M C, Astruc D: Gold nanoparticles: assembly, supramolecular chemistry, quantum-size-related properties, and applications toward biology, catalysis, and nanotechnology. *Chem Rev* 2004, 104:293-346.

40. Peer D, Karp J M, Hong S, Farokhzad O C, Margalit R, Langer R: Nanocarriers as an emerging platform for cancer therapy. *Nat Nanotechnol* 2007, 2:751-760.

While certain embodiments have been illustrated and described, a person with ordinary skill in the art, after reading the foregoing specification, can effect changes, substitutions of equivalents and other types of alterations to the nanoparticle compositions of the present technology as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles, and textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A method for treating a subject suffering from a RHAMM-positive cancer, wherein the method comprises administering to the subject an effective amount of the nanoparticle composition to treat the RHAMM-positive cancer; the nanoparticle composition comprising a plurality of nanoparticles where each nanoparticle comprises
a particle core with an outer surface;
a first layer coating the outer surface of the particle core, the first layer comprising one or both of poly-L-lysine and poly-L-arginine and optionally comprising a fluorescent dye;

a second layer coating the first layer, the second layer comprising one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1);
a third layer coating the second layer, the third layer comprising an apoptotic peptide and optionally comprising a fluorescent dye; and
a fourth layer coating the third layer, the fourth layer comprising hyaluronic acid or a pharmaceutically acceptable salt thereof, and
wherein the plurality of nanoparticles has an intensity-weighted average diameter as determined by dynamic light scattering from about 100 nm to about 300 nm.

B. The method of Paragraph A, wherein the RHAMM-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

C. The method of Paragraph A or Paragraph B, wherein the RHAMM-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

D. The method of any one of Paragraphs A-C, wherein the RHAMM-positive cancer is a metastatic cancer.

E. The method of any one of Paragraphs A-D, wherein a solid tumor in the subject comprises the RHAMM-positive cancer.

F. The method of any one of Paragraphs A-E, wherein the RHAMM-positive cancer overexpresses RHAMM.

G. The method of any one of Paragraphs A-F, wherein the RHAMM-positive cancer is a $RHAMM^B$-positive cancer.

H. The method of Paragraph G, wherein the $RHAMM^B$-positive cancer overexpresses $RHAMM^B$.

I. The method of Paragraph G or Paragraph H, wherein the $RHAMM^B$-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

J. The method of any one of Paragraphs G-I, wherein the $RHAMM^B$-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

K. The method of any one of Paragraphs G-J, wherein the RHAMM$^B$-positive cancer is a metastatic cancer.

L. The method of any one of Paragraphs G-K, wherein a solid tumor in the subject comprises the RHAMM$^B$-positive cancer.

M. The method of any one of Paragraphs A-L, wherein the subject is a mammal.

N. The method of any one of Paragraphs A-M, wherein the subject is human.

O. The method of any one of Paragraphs A-N, wherein administering to the subject the effective amount of the nanoparticle composition to treat the RHAMM-positive cancer comprises one or both of intravenous administration and intratumoral administration.

P. The method of any one of Paragraphs A-O, wherein the nanoparticle composition does not comprise a fluorescent dye.

Q. The method of any one of Paragraphs A-P, wherein the particle core is a gold particle core, where the gold particle core in the plurality of nanoparticles has an intensity-weighted average diameter as determined by dynamic light scattering from about 30 nm to about 50 nm.

R. The method of any one of Paragraphs A-Q, wherein first layer has an average thickness of about 30 nm to about 40 nm.

S. The method of any one of Paragraphs A-R, wherein the first layer comprises poly-L-lysine with a weight-average molecular weight of about 30,000 to about 70,000.

T. The method of any one of Paragraphs A-S, wherein the second layer has an average thickness of about 6 nm to about 20 nm.

U. The method of any one of Paragraphs A-T, wherein the second layer comprises one or more siRNAs having the sequence of any one of

```
                                 (SEQ ID NO. 2)
5'-GGUAUUGGUGAGUCGGAUCdTdT-3', (SEQ ID NO. 3)
5'-GAUCCGACUCACCAAUACCdTdT-3', (SEQ ID NO. 16)
5'-CAGGGACAGCATATCAGAG-3', (SEQ ID NO. 17)
5'-CTCTGATATGCTGTCCCTG-3', (SEQ ID NO. 18)
5'-UCACUAAACUGACUCCAGCUGUAUC-3', (SEQ ID NO. 19)
5'-GAUACAGCUGGAGUCAGUUUAGUGA-3', (SEQ ID NO. 20)
5'-CCCAGUGCCAUCAAUGGCAACCCAU-3', (SEQ ID NO. 21)
5'-AUGGGUUGCCAUUGAUGGCACUGGG-3', (SEQ ID NO. 22)
5'-GCAGUUUGGAUGCCCGGGAGGUGAU-3',
```

-continued

```
                                 (SEQ ID NO. 23)
5'-AUCACCUCCCGGGCAUCCAAACUGC-3', (SEQ ID NO. 24)
5'-AACAGGGACAGCATATCAGAGCTdTdT-3', (SEQ ID NO. 25)
5'-AGCUCUGAUAUGCUGUCCCUGUUdTdT-3', (SEQ ID NO. 26)
5'-GGAGAUGCAGGUAUUGGUG-3', (SEQ ID NO. 27)
5'-CACCAAUACCUGCAUCUCC-3', (SEQ ID NO. 28)
5'-UGACCAGACACUGACCAUC-3', (SEQ ID NO. 29)
5'-GAUGGUCAGUGUCUGGUCA-3', (SEQ ID NO. 30)
5'-CAGGGACAGCAUAUCAGAGdTdT-3', (SEQ ID NO. 31)
5'-CUCUGAUAUGCUGUCCCUGdTdT-3', (SEQ ID NO. 32)
5'-AGUUUCGAGACUAUACGAC-3', (SEQ ID NO. 33)
5'-GUCGUAUAGUCUCGAAACU-3', (SEQ ID NO. 34)
5'-GCAGCUUGGAUGGCCACUUdTdT-3',
and (SEQ ID NO. 35)
5'-AAGUGGCCAUCCAAGCUGCdAdG-3'.
```

V. The method of any one of Paragraphs A-U, wherein the third layer has an average thickness of about 6 nm to about 20 nm.

W. The method of any one of Paragraphs A-V, where the third layer comprises one or more apoptotic peptides having the sequence of any one of

```
                                 (SEQ ID NO. 1)
KLAKLAKKLAKLAKKLAKLAKKLAKLAK, (SEQ ID NO. 6)
FLGALFKALSKLL, (SEQ ID NO. 7)
RAALAVVLGRGGPR, (SEQ ID NO. 8)
RDGDSCRGGGPV, (SEQ ID NO. 9)
THRPPMWSPVWPGGGKLLLKLLKKLLKLLKKK, (SEQ ID NO. 10)
c(LKLKKFKKLQ), (SEQ ID NO. 11)
CRGDCGGKWCFRVCYRGICYRRCR, (SEQ ID NO. 12)
GIGKFLHSAKKFGKAFVGEIMNS-NH₂, (SEQ ID NO. 13)
N-myristoyl-PSQSK(εN-4-bromobenzoyl)SK
(εN-4-bromobenzoyl)A,
```

-continued

```
                                          (SEQ ID NO. 14)
  A₉K,
  and (SEQ ID NO. 15)
  KLAKLAKKLAKLAKKLAKLAK.
```

X. The method of any one of Paragraphs A-W, wherein the fourth layer has an average thickness of about 10 nm to about 40 nm.

Y. The method of any one of Paragraphs A-X, wherein the fourth layer comprises sodium hyaluronate Z. The method of any one of Paragraphs A-Y, wherein the fourth layer comprises sodium hyaluronate with a weight-average molecular weight of about 100,000 to about 150,000.

AA. The method of any one of Paragraphs A-Z, wherein the nanoparticle composition further comprises water.

AB. A nanoparticle composition for use in treating a subject suffering from a RHAMM-positive cancer, the nanoparticle composition comprising a plurality of nanoparticles where each nanoparticle comprises
a particle core with an outer surface;
a first layer coating the outer surface of the particle core, the first layer comprising one or both of poly-L-lysine and poly-L-arginine and optionally comprising a fluorescent dye;
a second layer coating the first layer, the second layer comprising one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1);
a third layer coating the second layer, the third layer comprising an apoptotic peptide and optionally comprising a fluorescent dye; and
a fourth layer coating the third layer, the fourth layer comprising hyaluronic acid or a pharmaceutically acceptable salt thereof, and
wherein the plurality of nanoparticles has an intensity-weighted average diameter as determined by dynamic light scattering from about 100 nm to about 300 nm.

AC. The nanoparticle composition of Paragraph AB, wherein the RHAMM-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

AD. The nanoparticle composition of Paragraph AB or Paragraph AC, wherein the RHAMM-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

AE. The nanoparticle composition of any one of Paragraphs AB-AD, wherein the RHAMM-positive cancer is a metastatic cancer.

AF. The nanoparticle composition of any one of Paragraphs AB-AE, wherein a solid tumor in the subject comprises the RHAMM-positive cancer.

AG. The nanoparticle composition of any one of Paragraphs AB-AF, wherein the RHAMM-positive cancer overexpresses RHAMM.

AH. The nanoparticle composition of any one of Paragraphs AB-AG, wherein the RHAMM-positive cancer is a RHAMM$^B$-positive cancer.

AI. The nanoparticle composition of Paragraph AH, wherein the RHAMM$^B$-positive cancer overexpresses RHAMM$^B$.

AJ. The nanoparticle composition of Paragraph AH or Paragraph AI, wherein the RHAMM$^B$-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

AK. The nanoparticle composition of any one of Paragraphs AH-AJ, wherein the RHAMM$^B$-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

AL. The nanoparticle composition of any one of Paragraphs AH-AK, wherein the RHAMM$^B$-positive cancer is a metastatic cancer.

AM. The nanoparticle composition of any one of Paragraphs AH-AL, wherein a solid tumor in the subject comprises the RHAMM$^B$-positive cancer.

AN. The nanoparticle composition of any one of Paragraphs AB-AM, wherein the subject is a mammal.

AO. The nanoparticle composition of any one of Paragraphs AB-AN, wherein the subject is human.

AP. The nanoparticle composition of any one of Paragraphs AB-AO, wherein the nanoparticle composition is formulated for one or both of intravenous administration and intratumoral administration.

AQ. The nanoparticle composition of any one of Paragraphs AB-AP, wherein the nanoparticle composition does not comprise a fluorescent dye.

AR. The nanoparticle composition of any one of Paragraphs AB-AQ, wherein the particle core is a gold particle core, where the gold particle core in the plurality of nanoparticles has an intensity-weighted average diameter as determined by dynamic light scattering from about 30 nm to about 50 nm.

AS. The nanoparticle composition of any one of Paragraphs AB-AR, wherein first layer has an average thickness of about 30 nm to about 40 nm.

AT. The nanoparticle composition of any one of Paragraphs AB-AS, wherein the first layer comprises poly-L-lysine with a weight-average molecular weight of about 30,000 to about 70,000.

AU. The nanoparticle composition of any one of Paragraphs AB-AT, wherein the second layer has an average thickness of about 6 nm to about 20 nm.

AV. The nanoparticle composition of any one of Paragraphs AB-AU, wherein the second layer comprises one or more siRNAs having the sequence of any one of

```
                              (SEQ ID NO. 2)
5'-GGUAUUGGUGAGUCGGAUCdTdT-3', (SEQ ID NO. 3)
5'-GAUCCGACUCACCAAUACCdTdT-3', (SEQ ID NO. 16)
5'-CAGGGACAGCATATCAGAG-3', (SEQ ID NO. 17)
5'-CTCTGATATGCTGTCCCTG-3', (SEQ ID NO. 18)
5'-UCACUAAACUGACUCCAGCUGUAUC-3', (SEQ ID NO. 19)
5'-GAUACAGCUGGAGUCAGUUUAGUGA-3', (SEQ ID NO. 20)
5'-CCCAGUGCCAUCAAUGGCAACCCAU-3', (SEQ ID NO. 21)
5'-AUGGGUUGCCAUUGAUGGCACUGGG-3', (SEQ ID NO. 22)
5'-GCAGUUUGGAUGCCCGGGAGGUGAU-3', (SEQ ID NO. 23)
5'-AUCACCUCCCGGGCAUCCAAACUGC-3', (SEQ ID NO. 24)
5'-AACAGGGACAGCATATCAGAGCTdTdT-3', (SEQ ID NO. 25)
5'-AGCUCUGAUAUGCUGUCCCUGUUdTdT-3', (SEQ ID NO. 26)
5'-GGAGAUGCAGGUAUUGGUG-3', (SEQ ID NO. 27)
5'-CACCAAUACCUGCAUCUCC-3', (SEQ ID NO. 28)
5'-UGACCAGACACUGACCAUC-3', (SEQ ID NO. 29)
5'-GAUGGUCAGUGUCUGGUCA-3', (SEQ ID NO. 30)
5'-CAGGGACAGCAUAUCAGAGdTdT-3', (SEQ ID NO. 31)
5'-CUCUGAUAUGCUGUCCCUGdTdT-3', (SEQ ID NO. 32)
5'-AGUUUCGAGACUAUACGAC-3', (SEQ ID NO. 33)
5'-GUCGUAUAGUCUCGAAACU-3', (SEQ ID NO. 34)
5'-GCAGCUUGGAUGGCCACUUdTdT-3',
and (SEQ ID NO. 35)
5'-AAGUGGCCAUCCAAGCUGCdAdG-3'.
```

AW. The nanoparticle composition of any one of Paragraphs AB-AV, wherein the third layer has an average thickness of about 6 nm to about 20 nm.

AX. The nanoparticle composition of any one of Paragraphs AB-AW, where the third layer comprises one or more apoptotic peptides having the sequence of any one of

```
                              (SEQ ID NO. 1)
KLAKLAKKLAKLAKKLAKLAKKLAKLAK, (SEQ ID NO. 6)
FLGALFKALSKLL, (SEQ ID NO. 7)
RAALAVVLGRGGPR, (SEQ ID NO. 8)
RDGDSCRGGGPV, (SEQ ID NO. 9)
THRPPMWSPVWPGGGKLLLKLLKKLLKLLKKK, (SEQ ID NO. 10)
c(LKLKKFKKLQ), (SEQ ID NO. 11)
CRGDCGGKWCFRVCYRGICYRRCR, (SEQ ID NO. 12)
GIGKFLHSAKKFGKAFVGEIMNS-NH$_2$, (SEQ ID NO. 13)
N-myristoyl-PSQSK(∈N-4-bromobenzoyl)SK (∈N-4-bromobenzoyl)A, (SEQ ID NO. 14)
A$_9$K,
and (SEQ ID NO. 15)
KLAKLAKKLAKLAKKLAKLAK.
```

AY. The nanoparticle composition of any one of Paragraphs AB-AX, wherein the fourth layer has an average thickness of about 10 nm to about 40 nm.

AZ. The nanoparticle composition of any one of Paragraphs AB-AY, wherein the fourth layer comprises sodium hyaluronate BA. The nanoparticle composition of any one of Paragraphs AB-AZ, wherein the fourth layer comprises sodium hyaluronate with a weight-average molecular weight of about 100,000 to about 150,000.

BB. The nanoparticle composition of any one of Paragraphs AB-BA, wherein the nanoparticle composition further comprises water.

BC. A nanoparticle composition comprising a plurality of nanoparticles, each nanoparticle comprising a particle core with an outer surface;

a first layer coating the outer surface of the particle core, the first layer comprising one or both of poly-L-lysine and poly-L-arginine and optionally comprising a fluorescent dye;

a second layer coating the first layer, the second layer comprising one or more siRNA that inhibit expression of Bcl-2, inhibit expression of Bcl-xL (BCL2L1), inhibit expression of MCL1, inhibit expression of Bcl-w (BCL2L2), inhibit expression of Bcl-b (BCL2L10), and/or inhibit expression of BFL1 (BCL2A1);

a third layer coating the second layer, the third layer comprising an apoptotic peptide and optionally comprising a fluorescent dye; and a fourth layer coating the third layer, the fourth layer
comprising hyaluronic acid or a pharmaceutically
acceptable salt thereof, and wherein the plurality of nanoparticles has an intensity-
weighted average diameter as determined by
dynamic light scattering from about 100 nm to about
300 nm.

BD. The nanoparticle composition of Paragraph BC,
wherein the nanoparticle composition is formulated for
one or both of intravenous administration and intratu-
moral administration.

BE. The nanoparticle composition of Paragraphs BC or
Paragraphs BD, wherein the nanoparticle composition
does not comprise a fluorescent dye.

BF. The nanoparticle composition of any one of Para-
graphs BC-BE, wherein particle core is a gold particle
core, where the gold particle core in the plurality of
nanoparticles has an intensity-weighted average diam-
eter as determined by dynamic light scattering from
about 30 nm to about 50 nm.

BG. The nanoparticle composition of any one of Para-
graphs BC-BF, wherein first layer has an average
thickness of about 30 nm to about 40 nm.

BH. The nanoparticle composition of any one of Para-
graphs BC-BG, wherein the first layer comprises poly-
L-lysine with a weight-average molecular weight of
about 30,000 to about 70,000.

BI. The nanoparticle composition of any one of Para-
graphs BC-BH, wherein the second layer has an aver-
age thickness of about 6 nm to about 20 nm.

BJ. The nanoparticle composition of any one of Para-
graphs BC-BI, wherein the second layer comprises one
or more siRNAs having the sequence of any one of

```
                                      (SEQ ID NO. 2)
5'-GGUAUUGGUGAGUCGGAUCdTdT-3', (SEQ ID NO. 3)
5'-GAUCCGACUCACCAAUACCdTdT-3', (SEQ ID NO. 16)
5'-CAGGGACAGCATATCAGAG-3', (SEQ ID NO. 17)
5'-CTCTGATATGCTGTCCCTG-3', (SEQ ID NO. 18)
5'-UCACUAAACUGACUCCAGCUGUAUC-3', (SEQ ID NO. 19)
5'-GAUACAGCUGGAGUCAGUUUAGUGA-3', (SEQ ID NO. 20)
5'-CCCAGUGCCAUCAAUGGCAACCCAU-3', (SEQ ID NO. 21)
5'-AUGGGUUGCCAUUGAUGGCACUGGG-3', (SEQ ID NO. 22)
5'-GCAGUUUGGAUGCCCGGGAGGUGAU-3', (SEQ ID NO. 23)
5'-AUCACCUCCCGGGCAUCCAAACUGC-3', (SEQ ID NO. 24)
5'-AACAGGGACAGCATATCAGAGCTdTdT-3', (SEQ ID NO. 25)
5'-AGCUCUGAUAUGCUGUCCCUGUUdTdT-3', (SEQ ID NO. 26)
5'-GGAGAUGCAGGUAUUGGUG-3',
```

-continued

```
                                      (SEQ ID NO. 27)
5'-CACCAAUACCUGCAUCUCC-3', (SEQ ID NO. 28)
5'-UGACCAGACACUGACCAUC-3', (SEQ ID NO. 29)
5'-GAUGGUCAGUGUCUGGUCA-3', (SEQ ID NO. 30)
5'-CAGGGACAGCAUAUCAGAGdTdT-3', (SEQ ID NO. 31)
5'-CUCUGAUAUGCUGUCCCUGdTdT-3', (SEQ ID NO. 32)
5'-AGUUUCGAGACUAUACGAC-3', (SEQ ID NO. 33)
5'-GUCGUAUAGUCUCGAAACU-3', (SEQ ID NO. 34)
5'-GCAGCUUGGAUGGCCACUUdTdT-3',
and (SEQ ID NO. 35)
5'-AAGUGGCCAUCCAAGCUGCdAdG-3'.
```

BK. The nanoparticle composition of any one of Para-
graphs BC-BJ, wherein the third layer has an average
thickness of about 6 nm to about 20 nm.

BL. The nanoparticle composition of any one of Para-
graphs BC-BK, where the third layer comprises one or
more apoptotic peptides having the sequence of any
one of

```
                                      (SEQ ID NO. 1)
KLAKLAKKLAKLAKKLAKLAKKLAKLAK, (SEQ ID NO. 6)
FLGALFKALSKLL, (SEQ ID NO. 7)
RAALAVVLGRGGPR, (SEQ ID NO. 8)
RDGDSCRGGGPV, (SEQ ID NO. 9)
THRPPMWSPVWPGGGKLLLKLLKKLLKLLKKK, (SEQ ID NO. 10)
c(LKLKKFKKLQ), (SEQ ID NO. 11)
CRGDCGGKWCFRVCYRGICYRRCR, (SEQ ID NO. 12)
GIGKFLHSAKKFGKAFVGEIMNS-NH2, (SEQ ID NO. 13)
N-myristoyl-PSQSK(εN-4-bromobenzoyl)SK (εN-4-bromobenzoyl)A, (SEQ ID NO. 14)
A9K,
and (SEQ ID NO. 15)
KLAKLAKKLAKLAKKLAKLAK.
```

BM. The nanoparticle composition of any one of Para-
graphs BC-BL, wherein the fourth layer has an average
thickness of about 10 nm to about 40 nm.

BN. The nanoparticle composition of any one of Paragraphs BC-BM, wherein the fourth layer comprises sodium hyaluronate BO. The nanoparticle composition of any one of Paragraphs BC-BN, wherein the fourth layer comprises sodium hyaluronate with a weight-average molecular weight of about 100,000 to about 150,000.

BP. The nanoparticle composition of any one of Paragraphs BC-BO, wherein the nanoparticle composition further comprises a pharmaceutically acceptable carrier.

BQ. A pharmaceutical composition comprising a pharmaceutically acceptable carrier and an effective amount of a nanoparticle composition of any one of Paragraphs BC-BO to treat RHAMM-positive cancer in a subject.

BR. The pharmaceutical composition of Paragraph BQ, wherein the pharmaceutical composition is formulated for parenteral administration.

BS. The pharmaceutical composition of Paragraph BQ or Paragraph BR, wherein pharmaceutical composition is formulated for intravenous administration and/or intratumoral administration.

BT. The pharmaceutical composition of any one of Paragraphs BQ-BS, wherein the RHAMM-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

BU. The pharmaceutical composition of any one of Paragraphs BQ-BT, wherein the RHAMM-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

BV. The pharmaceutical composition of any one of Paragraphs BQ-BU, wherein the RHAMM-positive cancer is a metastatic cancer.

BW. The pharmaceutical composition of any one of Paragraphs BQ-BV, wherein a solid tumor in the subject comprises the RHAMM-positive cancer.

BX. The pharmaceutical composition of any one of Paragraphs BQ-BW, wherein the RHAMM-positive cancer overexpresses RHAMM.

BY. The pharmaceutical composition of any one of Paragraphs BQ-BX, wherein the RHAMM-positive cancer is a RHAMM$^B$-positive cancer.

BZ. The pharmaceutical composition of Paragraph BY, wherein the RHAMM$^B$-positive cancer overexpresses RHAMM$^B$.

CA. The pharmaceutical composition of Paragraph BY or Paragraph BZ, wherein the RHAMM$^B$-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

CB. The pharmaceutical composition of any one of Paragraphs BY-CA, wherein the RHAMM$^B$-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

CC. The pharmaceutical composition of any one of Paragraphs BY-CB, wherein the RHAMM$^B$-positive cancer is a metastatic cancer.

CD. The pharmaceutical composition of any one of Paragraphs BY-CC, wherein a solid tumor in the subject comprises the RHAMM$^B$-positive cancer.

CE. The pharmaceutical composition of any one of Paragraphs BQ-CD, wherein the subject is a mammal.

CF. The pharmaceutical composition of any one of Paragraphs BQ-CE, wherein the subject is human.

CG. A nanoparticle composition comprising a plurality of nanoparticles, each nanoparticle comprising
a particle core with an outer surface;
a first layer coating the outer surface of the particle core, the first layer comprising an apoptotic peptide and optionally comprising a fluorescent dye;
a second layer coating the first layer, the second layer comprising one or more siRNA that inhibit expression of Bcl-2, inhibit expression of Bcl-xL, inhibit expression of MCL1, inhibit expression of Bcl-w, inhibit expression of Bcl-b, and/or inhibit expression of BFL1;
a third layer coating the second layer, the third layer comprising one or both of poly-L-lysine and poly-L-arginine and optionally comprising a fluorescent dye; and
a fourth layer coating the third layer, the fourth layer comprising hyaluronic acid or a pharmaceutically acceptable salt thereof, and
wherein the plurality of nanoparticles has an intensity-weighted average diameter as determined by dynamic light scattering from about 100 nm to about 300 nm.

CH. The nanoparticle composition of Paragraph CG, wherein the nanoparticle composition is formulated for one or both of intravenous administration and intratumoral administration.

CI. The nanoparticle composition of Paragraph CG or Paragraph CH, wherein the nanoparticle composition does not comprise a fluorescent dye.

CJ. The nanoparticle composition of any one of Paragraphs CG-CI, wherein the particle core is a gold particle core, where the gold particle core in the plurality of nanoparticles has an intensity-weighted average diameter as determined by dynamic light scattering from about 30 nm to about 50 nm.

CK. The nanoparticle composition of any one of Paragraphs CG-CJ, wherein the first layer has an average thickness of about 6 nm to about 20 nm.

CL. The nanoparticle composition of any one of Paragraphs CG-CK, where the first layer comprises one or more apoptotic peptides having the sequence of any one of

```
                                      (SEQ ID NO. 1)
KLAKLAKKLAKLAKKLAKLAKKLAKLAK, (SEQ ID NO. 6)
FLGALFKALSKLL, (SEQ ID NO. 7)
RAALAVVLGRGGPR, (SEQ ID NO. 8)
RDGDSCRGGGPV, (SEQ ID NO. 9)
THRPPMWSPVWPGGGKLLLKLLKKLLKLLKKK, (SEQ ID NO. 10)
c(LKLKKFKKLQ), (SEQ ID NO. 11)
CRGDCGGKWCFRVCYRGICYRRCR, (SEQ ID NO. 12)
GIGKFLHSAKKFGKAFVGEIMNS-NH₂, (SEQ ID NO. 13)
N-myristoyl-PSQSK(ϵN-4-bromobenzoyl)SK (ϵN-4-bromobenzoyl)A, (SEQ ID NO. 14)
A₉K,
and (SEQ ID NO. 15)
KLAKLAKKLAKLAKKLAKLAK.
```

CM. The nanoparticle composition of any one of Paragraphs CG-CL, wherein the second layer has an average thickness of about 6 nm to about 20 nm.

CN. The nanoparticle composition of any one of Paragraphs CG-CM, wherein the second layer comprises one or more siRNAs having the sequence of any one of

```
                                      (SEQ ID NO. 2)
5'-GGUAUUGGUGAGUCGGAUCdTdT-3', (SEQ ID NO. 3)
5'-GAUCCGACUCACCAAUACCdTdT-3', (SEQ ID NO. 16)
5'-CAGGGACAGCATATCAGAG-3', (SEQ ID NO. 17)
5'-CTCTGATATGCTGTCCCTG-3', (SEQ ID NO. 18)
5'-UCACUAAACUGACUCCAGCUGUAUC-3', (SEQ ID NO. 19)
5'-GAUACAGCUGGAGUCAGUUUAGUGA-3', (SEQ ID NO. 20)
5'-CCCAGUGCCAUCAAUGGCAACCCAU-3', (SEQ ID NO. 21)
5'-AUGGGUUGCCAUUGAUGGCACUGGG-3', (SEQ ID NO. 22)
5'-GCAGUUUGGAUGCCCGGGAGGUGAU-3', (SEQ ID NO. 23)
5'-AUCACCUCCCGGGCAUCCAAACUGC-3',
```

-continued

```
                                      (SEQ ID NO. 24)
5'-AACAGGGACAGCATATCAGAGCTdTdT-3', (SEQ ID NO. 25)
5'-AGCUCUGAUAUGCUGUCCCUGUUdTdT-3', (SEQ ID NO. 26)
5'-GGAGAUGCAGGUAUUGGUG-3', (SEQ ID NO. 27)
5'-CACCAAUACCUGCAUCUCC-3', (SEQ ID NO. 28)
5'-UGACCAGACACUGACCAUC-3', (SEQ ID NO. 29)
5'-GAUGGUCAGUGUCUGGUCA-3', (SEQ ID NO. 30)
5'-CAGGGACAGCAUAUCAGAGdTdT-3', (SEQ ID NO. 31)
5'-CUCUGAUAUGCUGUCCCUGdTdT-3', (SEQ ID NO. 32)
5'-AGUUUCGAGACUAUACGAC-3', (SEQ ID NO. 33)
5'-GUCGUAUAGUCUCGAAACU-3', (SEQ ID NO. 34)
5'-GCAGCUUGGAUGGCCACUUdTdT-3',
and (SEQ ID NO. 35)
5'-AAGUGGCCAUCCAAGCUGCdAdG-3'.
```

CO. The nanoparticle composition of any one of Paragraphs CG-CN, wherein third layer has an average thickness of about 30 nm to about 40 nm.

CP. The nanoparticle composition of any one of Paragraphs CG-CO, wherein the third layer comprises poly-L-lysine with a weight-average molecular weight of about 30,000 to about 70,000.

CQ. The nanoparticle composition of any one of Paragraphs CG-CP, wherein the fourth layer has an average thickness of about 10 nm to about 40 nm.

CR. The nanoparticle composition of any one of Paragraphs CG-CQ, wherein the fourth layer comprises sodium hyaluronate CS. The nanoparticle composition of any one of Paragraphs CG-CR, wherein the fourth layer comprises sodium hyaluronate with a weight-average molecular weight of about 100,000 to about 150,000.

CT. The nanoparticle composition of any one of Paragraphs CG-CS, wherein the nanoparticle composition is for use in treating a RHAMM-positive cancer in a subject.

CU. The nanoparticle composition of any one of Paragraphs CG-CT, wherein the nanoparticle composition further comprises a pharmaceutically acceptable carrier.

CV. A pharmaceutical composition comprising a pharmaceutically acceptable carrier and an effective amount of a nanoparticle composition of any one of Paragraphs CG-CT to treat RHAMM-positive cancer in a subject.

CW. The pharmaceutical composition of Paragraph CV, wherein the pharmaceutical composition is formulated for parenteral administration.

CX. The pharmaceutical composition of Paragraph CV or Paragraph CW, wherein pharmaceutical composition is formulated for intravenous administration and/or intratumoral administration.

CY. The pharmaceutical composition of any one of Paragraphs CV-CX, wherein the RHAMM-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

CZ. The pharmaceutical composition of any one of Paragraphs CV-CY, wherein the RHAMM-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

DA. The pharmaceutical composition of any one of Paragraphs CV-CZ, wherein the RHAMM-positive cancer is a metastatic cancer.

DB. The pharmaceutical composition of any one of Paragraphs CV-DA, wherein a solid tumor in the subject comprises the RHAMM-positive cancer.

DC. The pharmaceutical composition of any one of Paragraphs CV-DB, wherein the RHAMM-positive cancer overexpresses RHAMM.

DD. The pharmaceutical composition of any one of Paragraphs CV-DC, wherein the RHAMM-positive cancer is a RHAMM$^B$-positive cancer.

DE. The pharmaceutical composition of Paragraph DD, wherein the RHAMM$^B$-positive cancer overexpresses RHAMM$^B$.

DF. The pharmaceutical composition of Paragraph DD or Paragraph DE, wherein the RHAMM$^B$-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

DG. The pharmaceutical composition of any one of Paragraphs DD-DF, wherein the RHAMM$^B$-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

DH. The pharmaceutical composition of any one of Paragraphs DD-DG, wherein the RHAMM$^B$-positive cancer is a metastatic cancer.

DI. The pharmaceutical composition of any one of Paragraphs DD-DH, wherein a solid tumor in the subject comprises the RHAMM$^B$-positive cancer.

DJ. The pharmaceutical composition of any one of Paragraphs CV-DI, wherein the subject is a mammal.

DK. The pharmaceutical composition of any one of Paragraphs CV-DJ, wherein the subject is human.

DL. A method for treating a subject suffering from a RHAMM-positive cancer, wherein the method comprises administering to the subject an effective amount of a nanoparticle composition of any one of Paragraphs CG-CU to treat the RHAMM-positive cancer.

DM. The method of Paragraph DL, wherein the RHAMM-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

DN. The method of Paragraph DL or Paragraph DM, wherein the RHAMM-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

DO. The method of any one of Paragraphs DL-DN, wherein the RHAMM-positive cancer is a metastatic cancer.

DP. The method of any one of Paragraphs DL-DO, wherein a solid tumor in the subject comprises the RHAMM-positive cancer.

DQ. The method of any one of Paragraphs DL-DP, wherein the RHAMM-positive cancer overexpresses RHAMM.

DR. The method of any one of Paragraphs DL-DQ, wherein the RHAMM-positive cancer is a RHAMM$^B$-positive cancer.

DS. The method of Paragraph DR, wherein the RHAMM$^B$-positive cancer overexpresses RHAMM$^B$.

DT. The method of Paragraph DR or Paragraph DS, wherein the RHAMM$^B$-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

DU. The method of any one of Paragraphs DR-DT, wherein the RHAMM$^B$-positive cancer is a pancreatic neuroendocrine tumor, a lung adenocarcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

DV. The method of any one of Paragraphs DR-DU, wherein the RHAMM$^B$-positive cancer is a metastatic cancer.

DW. The method of any one of Paragraphs DR-DV, wherein a solid tumor in the subject comprises the RHAMM$^B$-positive cancer.

DX. The method of any one of Paragraphs DL-DW, wherein the subject is a mammal.

DY. The method of any one of Paragraphs DL-DX, wherein the subject is human.

Other embodiments are set forth in the following claims, along with the full scope of equivalents to which such claims are entitled.

---

The invention claimed is:

1. A method for treating a subject suffering from a RHAMM-positive cancer, wherein the method comprises administering to the subject an effective amount of a nanoparticle composition to treat the RHAMM-positive cancer; the nanoparticle composition comprising a plurality of nanoparticles where each nanoparticle comprises a particle core with an outer surface;

a first layer coating the outer surface of the particle core, the first layer comprising poly-L-lysine with a weight-average molecular weight of about 40,000 to about 70,000 and optionally comprising poly-L-arginine and optionally comprising a fluorescent dye;

a second layer coating the first layer, the second layer comprising one or more siRNA that inhibit expression of Bcl-xL, inhibit expression of MCL1, inhibit expression of Bcl-w, inhibit expression of Bcl-b, and/or inhibit expression of BFL1, wherein the siRNA has the sequence of 5'-GGUAUUGGUGAGUCGGAUCdTdT-3' (SEQ ID NO. 2) or 5'-GAUCCGACUCAC-CAAUACCdTdT-3' (SEQ ID NO. 3);

a third layer coating the second layer, the third layer comprising an apoptotic peptide having the sequence of KLAKLAKKLAKLAKKLAKLAKKLAKLAK (SEQ ID NO. 1), and optionally comprising a fluorescent dye; and a fourth layer coating the third layer, the fourth layer comprising hyaluronic acid or a pharmaceutically acceptable salt thereof; and wherein the plurality of nanoparticles has an intensity-weighted average diameter as determined by dynamic light scattering from about 100 nm to about 300 nm.

2. The method of claim 1, wherein the RHAMM-positive cancer is a RHAMM$^B$-positive cancer.

3. The method of claim 2, wherein the RHAMM$^B$-positive cancer comprises one or more of a colon cancer, a colorectal cancer, a gastric cancer, an endometrial cancer, a prostate cancer, a breast cancer, a brain cancer, an ovarian cancer, a pancreatic cancer, and a lung cancer.

4. The method of claim 2, wherein the RHAMM$^B$-positive cancer is a pancreatic neuroendocrine tumor, a lung adeno-carcinoma, a squamous lung carcinoma, non-small cell lung cancer, small cell carcinoma of the lung, bladder cancer, colon cancer, gallbladder cancer, pancreatic cancer, esophageal cancer, melanoma, liver cancer, primary gastric adenocarcinoma, primary colorectal adenocarcinoma, renal cell carcinoma, prostate cancer (such as castration resistant prostate cancer), a neuroendocrine tumor, a pituitary tumor, a vasoactive intestinal peptide-secreting tumor, a glioma, breast cancer, an adrenal cortical cancer, a cervical carcinoma, a vulvar carcinoma, an endometrial carcinoma, a primary ovarian carcinoma, a metastatic ovarian carcinoma, a serous carcinoma, or a combination of any two or more thereof.

5. A nanoparticle composition comprising a plurality of nanoparticles, each nanoparticle comprising a particle core with an outer surface;

a first layer coating the outer surface of the particle core, the first layer comprising poly-L-lysine with a weight-average molecular weight of about 40,000 to about 70,000 and optionally comprising poly-L-arginine and optionally comprising a fluorescent dye;

a second layer coating the first layer, the second layer comprising one or more siRNA that inhibit expression of Bcl-xL, inhibit expression of MCL1, inhibit expression of Bcl-w, inhibit expression of Bcl-b, and/or inhibit expression of BFL1, wherein the siRNA has the sequence of 5'-GGUAUUGGUGAGUCGGAUCdTdT-3' (SEQ ID NO. 2) or 5'-GAUCCGACUCAC-CAAUACCdTdT-3' (SEQ ID NO. 3);

a third layer coating the second layer, the third layer comprising an apoptotic peptide having the sequence of KLAKLAKKLAKLAKKLAKLAKKLAKLAK (SEQ ID NO. 1) and optionally comprising a fluorescent dye; and a fourth layer coating the third layer, the fourth layer comprising hyaluronic acid or a pharmaceutically acceptable salt thereof; and wherein the plurality of nanoparticles has an intensity-weighted average diameter as determined by dynamic light scattering from about 100 nm to about 300 nm.

6. The nanoparticle composition of claim 5, wherein the nanoparticle composition is formulated for one or both of intravenous administration and intratumoral administration.

7. The nanoparticle composition of claim 5, wherein the particle core is a gold particle core, where the gold particle core in the plurality of nanoparticles has an intensity-weighted average diameter as determined by dynamic light scattering from about 30 nm to about 50 nm.

8. The nanoparticle composition of claim 5, wherein first layer has an average thickness of about 30 nm to about 40 nm.

9. The nanoparticle composition of claim 5, wherein the second layer has an average thickness of about 6 nm to about 20 nm.

10. The nanoparticle composition of claim 5, wherein the third layer has an average thickness of about 6 nm to about 20 nm.

11. The nanoparticle composition of claim 5, wherein the fourth layer has an average thickness of about 10 nm to about 40 nm.

12. The nanoparticle composition of claim 5, wherein the fourth layer comprises sodium hyaluronate.

13. The nanoparticle composition of claim 5, wherein the fourth layer comprises sodium hyaluronate with a weight-average molecular weight of about 100,000 to about 150,000.

14. A pharmaceutical composition comprising a pharmaceutically acceptable carrier and an effective amount of a nanoparticle composition of claim 5 to treat RHAMM-positive cancer in a subject.

15. A nanoparticle composition comprising a plurality of nanoparticles, each nanoparticle comprising a particle core with an outer surface;

a first layer coating the outer surface of the particle core, the first layer comprising an apoptotic peptide having the sequence of KLAKLAKKLAKLAKKLAK-LAKKLAKLAK (SEQ ID NO. 1) and optionally comprising a fluorescent dye;

a second layer coating the first layer, the second layer comprising one or more siRNA that inhibit expression of Bcl-xL, inhibit expression of MCL1, inhibit expression of Bcl-w, inhibit expression of Bcl-b, and/or inhibit expression of BFL1, wherein the siRNA has the sequence of 5'-GGUAUUGGUGAGUCGGAUCdTdT-3' (SEQ ID NO. 2) or 5'-GAUCCGACUCAC-CAAUACCdTdT-3' (SEQ ID NO. 3);

a third layer coating the second layer, the third layer comprising poly-L-lysine with a weight-average molecular weight of about 40,000 to about 70,000 and optionally comprising poly-L-arginine and optionally comprising a fluorescent dye; and a fourth layer coating the third layer, the fourth layer comprising hyaluronic acid or a pharmaceutically acceptable salt thereof; and wherein the plurality of nanoparticles has an intensity-weighted average diameter as determined by dynamic light scattering from about 100 nm to about 300 nm.

16. A pharmaceutical composition comprising a pharmaceutically acceptable carrier and an effective amount of a nanoparticle composition of claim 15 to treat RHAMM-positive cancer in a subject.

17. A method for treating a subject suffering from a RHAMM-positive cancer, wherein the method comprises administering to the subject an effective amount of a nanoparticle composition of claim 15 to treat the RHAMM-positive cancer.

18. The method of claim 1, consisting of administering to the subject an effective amount of a nanoparticle composition to treat the RHAMM-positive cancer; the nanoparticle composition comprising a plurality of nanoparticles where each nanoparticle comprises a particle core with an outer surface;

a first layer coating the outer surface of the particle core, the first layer comprising poly-L-lysine with a weight-average molecular weight of about 40,000 to about 70,000 and optionally comprising poly-L-arginine and optionally comprising a fluorescent dye;

a second layer coating the first layer, the second layer comprising one or more siRNA that inhibit expression of Bcl-XL, inhibit expression of MCL1, inhibit expression of Bcl-w, inhibit expression of Bcl-b, and/or inhibit expression of BFL1, wherein the siRNA has the sequence of 5'-GGUAUUGGUGAGUCGGAUCdTdT-3' (SEQ ID NO. 2) or 5'-GAUCCGACUCAC-CAAUACCdTdT-3' (SEQ ID NO. 3);

a third layer coating the second layer, the third layer comprising an apoptotic peptide having the sequence of KLAKLAKKLAKLAKKLAKLAKKLAKLAK (SEQ ID NO. 1), and optionally comprising a fluorescent dye; and a fourth layer coating the third layer, the fourth layer comprising hyaluronic acid or a pharmaceutically acceptable salt thereof; and wherein the plurality of nanoparticles has an intensity-weighted average diameter as determined by dynamic light scattering from about 100 nm to about 300 nm.

19. The nanoparticle composition of claim 5, each nanoparticle consisting of a particle core with an outer surface;

a first layer coating the outer surface of the particle core, the first layer comprising poly-L-lysine with a weight-average molecular weight of about 40,000 to about 70,000 and optionally comprising poly-L-arginine and optionally comprising a fluorescent dye;

a second layer coating the first layer, the second layer comprising one or more siRNA that inhibit expression of Bcl-xL, inhibit expression of MCL1, inhibit expression of Bcl-w, inhibit expression of Bcl-b, and/or inhibit expression of BFL1, wherein the siRNA has the sequence of 5'-GGUAUUGGUGAGUCGGAUCdTdT-3' (SEQ ID NO. 2) or 5'-GAUCCGACUCAC-CAAUACCdTdT-3' (SEQ ID NO. 3);

a third layer coating the second layer, the third layer comprising an apoptotic peptide having the sequence of KLAKLAKKLAKLAKKLAKLAKKLAKLAK (SEQ ID NO. 1) and optionally comprising a fluorescent dye; and a fourth layer coating the third layer, the fourth layer comprising hyaluronic acid or a pharmaceutically acceptable salt thereof; and wherein the plurality of nanoparticles has an intensity-weighted average diameter as determined by dynamic light scattering from about 100 nm to about 300 nm.

20. The nanoparticle composition of claim 15, each nanoparticle consisting of a particle core with an outer surface;

a first layer coating the outer surface of the particle core, the first layer comprising an apoptotic peptide having the sequence of KLAKLAKKLAKLAKKLAK-LAKKLAKLAK (SEQ ID NO. 1) and optionally comprising a fluorescent dye;

a second layer coating the first layer, the second layer comprising one or more siRNA that inhibit expression of Bcl-XL, inhibit expression of MCL1, inhibit expression of Bcl-w, inhibit expression of Bcl-b, and/or inhibit expression of BFL1, wherein the siRNA has the sequence of 5'-GGUAUUGGUGAGUCGGAUCdTdT-3' (SEQ ID NO. 2) or 5'-GAUCCGACUCAC-CAAUACCdTdT-3' (SEQ ID NO. 3);

a third layer coating the second layer, the third layer comprising poly-L-lysine with a weight-average molecular weight of about 40,000 to about 70,000 and optionally comprising poly-L-arginine and optionally comprising a fluorescent dye; and a fourth layer coating the third layer, the fourth layer comprising hyaluronic acid or a pharmaceutically acceptable salt thereof; and wherein the plurality of nanoparticles has an intensity-weighted average diameter as determined by dynamic light scattering from about 100 nm to about 300 nm.

* * * * *

```
                          SEQUENCE LISTING

<160> NUMBER OF SEQ ID NOS: 35

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Ala Lys Leu Ala Lys Lys Leu Ala Lys Leu Ala Lys Lys Leu
1               5                   10                  15

Ala Lys Leu Ala Lys Lys Leu Ala Lys Leu Ala Lys
            20                  25

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gguauuggug agucggauct t                                            21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gauccgacuc accaauacct t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uagggguugc gacguuuagt t                                            21

<210> SEQ ID NO 5
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
cuaaacgucg caaccccuat t                                          21

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Leu Gly Ala Leu Phe Lys Ala Leu Ser Lys Leu Leu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ala Leu Ala Val Val Leu Gly Arg Gly Gly Pro Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Asp Gly Asp Ser Cys Arg Gly Gly Gly Pro Val
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Thr His Arg Pro Pro Met Trp Ser Pro Val Trp Pro Gly Gly Gly Lys
1               5                   10                  15

Leu Leu Leu Lys Leu Leu Lys Lys Leu Leu Lys Leu Leu Lys Lys Lys
            20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 10

Leu Lys Leu Lys Lys Phe Lys Lys Leu Gln
1               5                   10

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Arg Gly Asp Cys Gly Gly Lys Trp Cys Phe Arg Val Cys Tyr Arg
1               5                   10                  15

Gly Ile Cys Tyr Arg Arg Cys Arg
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-myristoyl-Pro
<220> FEATURE:
<221> NAME/KEY: MOD_RES
<222> LOCATION: (5)..(5)
<223> OTHER INFORMATION: Lys(epsilonN-4-bromobenzoyl)
<220> FEATURE:
<221> NAME/KEY: MOD_RES
<222> LOCATION: (7)..(7)
<223> OTHER INFORMATION: Lys(epsilonN-4-bromobenzoyl)

<400> SEQUENCE: 13

Pro Ser Gln Ser Lys Ser Lys Ala
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala Ala Ala Ala Ala Ala Ala Lys
1               5                   10
```

```
<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Ala Lys Leu Ala Lys Lys Leu Ala Lys Leu Ala Lys Lys Leu
1               5                   10                  15

Ala Lys Leu Ala Lys
            20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cagggacagc atatcagag                                               19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctctgatatg ctgtccctg                                               19

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ucacuaaacu gacuccagcu guauc                                        25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gauacagcug gagucaguuu aguga                                        25

<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
```

-continued cccagugcca ucaauggcaa cccau                                                      25

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auggguugcc auugauggca cuggg                                                      25

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gcaguuugga ugcccgggag gugau                                                      25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aucaccuccc gggcauccaa acugc                                                      25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aacagggaca gcatatcaga gcttt                                                      25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
agcucugaua ugcugucccu guutt                                                      25

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 26
ggagaugcag guauuggug                                                                        19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
caccaauacc ugcaucucc                                                                        19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugaccagaca cugaccauc                                                                        19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gauggucagu gucugguca                                                                        19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
cagggacagc auaucagagt t                                                                     21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
cucugauaug cugucccugt t                                                                     21

<210> SEQ ID NO 32
<211> LENGTH: 19

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
aguuucgaga cuauacgac                                                      19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gucguauagu cucgaaacu                                                      19

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
gcagcuugga uggccacuut t                                                   21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aaguggccau ccaagcugca g                                                   21
```